United States Patent
Duefel et al.

(10) Patent No.: US 11,491,236 B2
(45) Date of Patent: Nov. 8, 2022

(54) COPY PROTECTION FOR ANTIBODIES

(71) Applicant: Roche Diagnostics Operations, Inc., Indianapolis, IN (US)

(72) Inventors: Harmut Duefel, Schlehdorf (DE); Uwe Kobold, Weilheim (DE); Andreas Leinenbach, Oberhausen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 285 days.

(21) Appl. No.: 16/852,931

(22) Filed: Apr. 20, 2020

(65) Prior Publication Data

US 2020/0246476 A1 Aug. 6, 2020

Related U.S. Application Data

(63) Continuation of application No. PCT/EP2018/078720, filed on Oct. 19, 2018.

(30) Foreign Application Priority Data

Oct. 20, 2017 (EP) .................... 17197603

(51) Int. Cl.
*A61K 47/68* (2017.01)
*G01N 33/68* (2006.01)
*G01N 30/88* (2006.01)

(52) U.S. Cl.
CPC ......... *A61K 47/68* (2017.08); *G01N 33/6848* (2013.01); *G01N 2030/8868* (2013.01); *G01N 2458/00* (2013.01)

(58) Field of Classification Search
CPC .............. A61K 47/68; G01N 33/6848; G01N 2030/8868; G01N 2458/00;
(Continued)

(56) References Cited

U.S. PATENT DOCUMENTS

| 4,275,149 A | 6/1981 | Litman et al. |
| 4,318,980 A | 3/1982 | Boguslaski et al. |

(Continued)

FOREIGN PATENT DOCUMENTS

| JP | 2003-96098 A | 4/2003 |
| JP | 2014-519029 A | 8/2014 |

(Continued)

OTHER PUBLICATIONS

Amsler, Phillip et al., Production and application of high quality stable isotope-labeled human immunoglobulin G1 for mass spectrometry analysis, Journal of Labelled Compounds and Radiopharmaceuticals, 2017, pp. 160-167, vol. 60, No. 3.

(Continued)

*Primary Examiner* — Kiet T Nguyen
(74) *Attorney, Agent, or Firm* — Stinson LLP

(57) ABSTRACT

The present disclosure is directed at an antibody conjugate having an antibody and a tag, wherein one or more element(s) present in the antibody exhibit an isotope ratio which differs from the naturally occurring isotope ratio of the one or more element(s), wherein the amount of the isotope which is less-common in nature, is increased to at least 4% of the atoms of the respective element in the antibody, as well as uses thereof.

Figure 2:
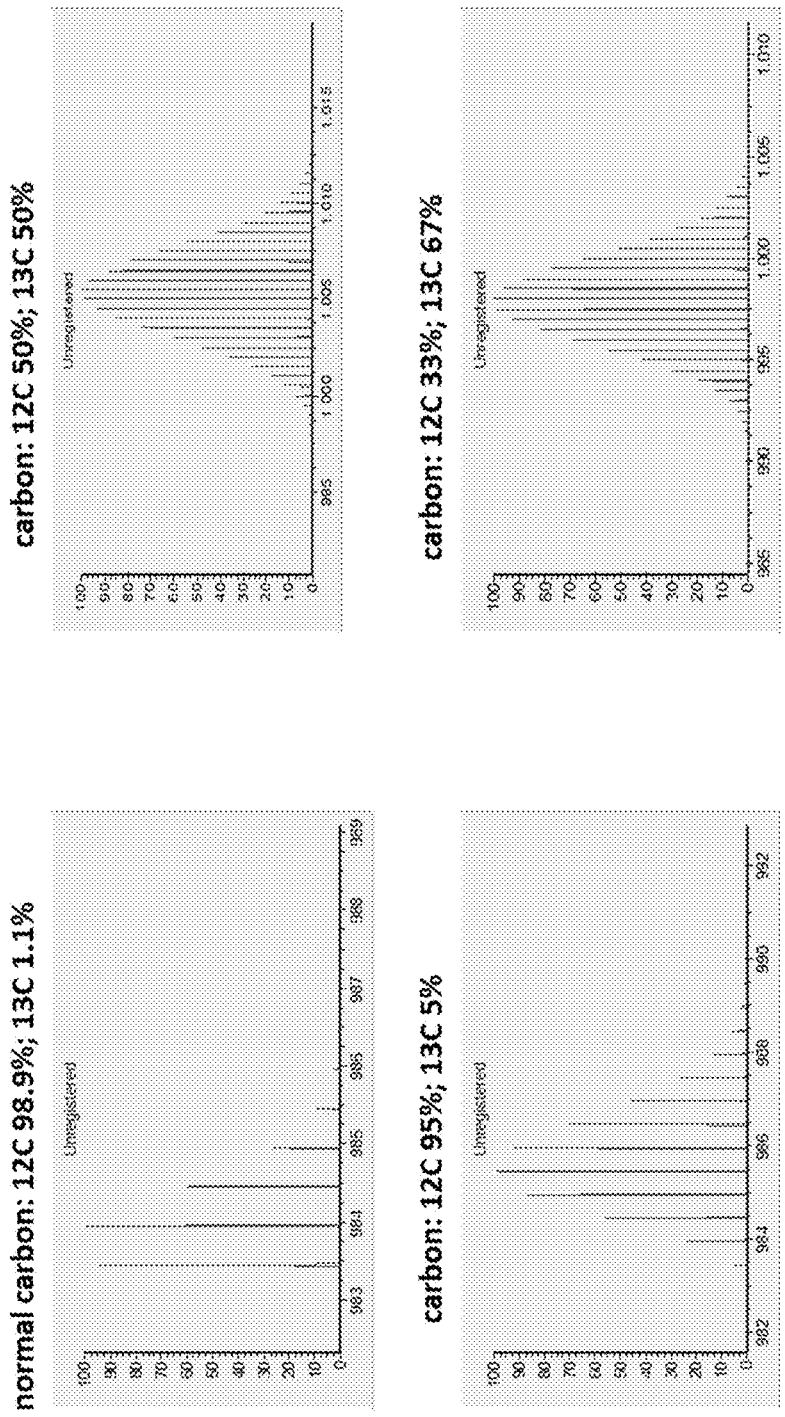

13 Claims, 5 Drawing Sheets
Specification includes a Sequence Listing.

(58) Field of Classification Search
CPC ............ G01N 2458/15; C07K 2317/10; C07K 2317/14; C07K 16/00
USPC ...................................................... 530/387.1
See application file for complete search history.

(56) References Cited

U.S. PATENT DOCUMENTS

| | | | |
|---|---|---|---|
| 4,737,456 | A | 4/1988 | Weng et al. |
| 5,098,846 | A * | 3/1992 | Fleming ............ G01N 33/54393 436/163 |
| 5,316,757 | A | 5/1994 | Sherry et al. |
| 5,342,606 | A | 8/1994 | Sherry et al. |
| 5,385,893 | A | 1/1995 | Kiefer |
| 5,428,139 | A | 6/1995 | Kiefer et al. |
| 5,428,155 | A | 6/1995 | Sherry et al. |
| 5,462,725 | A | 10/1995 | Kiefer et al. |
| 5,480,990 | A | 1/1996 | Kiefer et al. |
| 5,739,294 | A | 4/1998 | Kiefer et al. |
| 5,750,660 | A | 5/1998 | Kiefer et al. |
| 5,834,456 | A | 11/1998 | Kiefer et al. |
| 2002/0090652 | A1 | 7/2002 | Fu et al. |
| 2004/0101920 | A1 | 5/2004 | Radziejewski et al. |
| 2007/0099251 | A1 * | 5/2007 | Zhang .................. G01N 33/574 435/7.92 |
| 2011/0111856 | A1 | 5/2011 | White et al. |
| 2012/0178183 | A1 * | 7/2012 | Nolan ...................... B82Y 5/00 530/367 |
| 2016/0331793 | A1 | 11/2016 | Champion et al. |

FOREIGN PATENT DOCUMENTS

| | | |
|---|---|---|
| WO | 1993/021232 A1 | 10/1993 |
| WO | 1994/011026 A2 | 5/1994 |
| WO | 2005/101017 A1 | 10/2005 |
| WO | 2011/032994 A1 | 3/2011 |
| WO | 2012/028697 A1 | 3/2012 |
| WO | 2012/107419 A1 | 8/2012 |
| WO | 2012155019 A1 | 11/2012 |

OTHER PUBLICATIONS

Anonymous, Labelled Trastuzumab 13C15N Absolute quantification of Herceptin® or its biosimilars, Promise Advanced Proteomics, 2018, Retrieved from the Internet: URL://promise-proteomics.com/product/sil-trastuzumab-13c15n, 8 pp.

Anonymous, SILu TM MAB Stable-Isotope Labeled Universal Monoclonal Antibody Standard human-recombinant, expressed in CHO cells, Sigma Aldrich Online Catalogue, 2018, Retrieved from http://www.sigmaaldrich.com/catalog/product/sigma/msqc3, 6 pp.

Bandeira, Nuno et al., Automated de novo protein sequencing of monoclonal antibodies, Nature Biotechnology, 2008, pp. 1336-1338, vol. 26, No. 12.

Blend, Michael J. et al., Labeling anti-HER2/neu Monoclonal Antibodies with 111In and 90Y Using a Bifunctional DTPA Chelating Agent, Cancer Biotherapy & Radiopharmaceuticals, 2003, pp. 355-363, vol. 18, No. 3.

Briggs, Mark S. J. et al., Synthesis of functionalised fluorescent dyes and their coupling to amines and amino acids, Journal of the American Chemical Society, Perkin Trans. 1, 1997, pp. 1051-1058.

Brinkley, Michael, A Brief Survey of Methods for Preparing Protein Conjugates with Dyes, Haptens, and Cross-Linking Reagents, Bioconjugate Chemistry, 1992, pp. 2-13, vol. 3.

Camera, Luigi et al., Evaluation of the Serum Stability and In Vivo Biodistribution of CHX-DTPA and Other Ligands for Yttrium Labeling of Monoclonal Antibodies, Journal of Nuclear Medicine, 1994, pp. 882-889, vol. 35.

Chen, Kang et al., Immunoglobulin D enhances immune surveillance by activating antimicrobial, proinflammatory and B cell-stimulating programs in basophils, Nature Immunology, 2009, pp. 889-898, vol. 10.

Chen, Yvonne et al., Selection and Analysis of an Optimized Anti-VEGF Antibody: Crystal Structure of an Affinity-matured Fab in Complex with Antigen, Journal of Molecular Biology, 1999, pp. 865-881, vol. 293.

Chothia, Cyrus and Lesk, Arthur M., Canonical Structures for the Hypervariable Regions of Immunoglobulins, Journal of Molecular Biology, 1987, pp. 901-917, vol. 196.

De León-Rodriquez, Luis M. et al., Solid-Phase Synthesis of DOTA-Peptides, Chemistry—A European Journal, 2004, pp. 1149-1155, vol. 10.

Denardo, Gerald L. et al., Comparison of 1,4,7,10-Tetraazacyclododecane-N,N',N",N"'-tetraacetic acid (DOTA)-Peptide-ChL6, a Novel Immunoconjugate with Catabolizable Linker, to 2-Iminothiolane-2-[p-(Bromoacetamido)benzyl]-DOTA-ChL6 in Breast Cancer Xenografts, Clinical Cancer Research, 1998, pp. 2483-2490, vol. 4.

Desmyter, Aline et al., Crystal structure of a camel single-domain VH antibody fragment in complex with lysozyme, Nature Structural Biology, 1996, pp. 803-811, vol. 3, No. 9.

Dodeigne, C. et al., Chemiluminescence as diagnostic tool. A review, Talanta, 2000, pp. 415-439, vol. 51.

Ellman, Jon et al., Biosynthetic Method for Introducing Unnatural Amino Acids Site-Specifically into Proteins, Methods in Enzymology, 1991, pp. 301-336, vol. 202.

Flatman, Stephen et al., Process analytics for purification of monoclonal antibodies, Journal of Chromatography B, 2007, pp. 79-87, vol. 848.

Fraker, Pamela J. and Speck, John C. Jr., Protein and Cell Membrane Iodinations with a Sparingly Soluble Chloroamide, 1,3,4,6-Tetrachloro-3a,6a-Diphenylglycoluril, Biochemical and Biophysical Research Communications, 1978, pp. 849-857, vol. 80, No. 4.

Geisberger, Roland et al., The riddle of the dual expression of IgM and IgD, Immunology, 2006, pp. 429-437, vol. 118.

Hnatowich, D.J. et al., The Preparation of DTPA-Coupled Antibodies Radiolabeled with Metallic Radionuclides: an Improved Method, Journal of Immunological Methods, 1983, pp. 147-157, vol. 65.

Hochleitner, Elisabeth O. et al., Characterization of a discontinuous epitope of the human immunodeficiency virus (HIV) core protein p24 by epitope excision and differential chemical modification followed by mass spectrometric peptide mapping analysis, Protein Science, 2000, pp. 487-496, Abstract only, vol. 9, Issue 3.

Huston, James S. et al., Protein engineering of antibody binding sites: Recovery of specific activity in an anti-digoxin single-chain Fv analogue produced in *Escherichia coli*, Proceedings of the National Academy of Sciences USA, 1988, pp. 5879-5883, vol. 85.

Ibba, Michael and Söll, Dieter, Genetic Code: Introducing Pyrrolysine, Current Biology, 2002, pp. R464-R466, vol. 12.

International Search Report dated Jan. 3, 2019, in Application No. PCT/EP2018/078720, 5 pp.

Izard, M. E. et al., An Improved Method for Labeling Monoclonal Antibodies with Samarium-153: Use of the Bifunctional Chelate 2-(p-Isothiocyanatobenzyl)-6-methyldiethylenetriaminepentaacetic Acid, Bioconjugate Chemistry, 1992, pp. 346-350, vol. 3.

Janeway, Charles A. Jr. and Travers, Paul, Structural variation in immunoglobulin constant regions. Structure of the Antibody Molecule and Immunoglobulin Genes, Immunobiology: The Immune System in Health and Disease, 1994, pp. 3:29-3:30, Current Biology Ltd., London.

Junghans, R. P. et al., Anti-Tac-H, a Humanized Antibody to the Interleukin 2 Receptor with New Features for Immunotherapy in Malignant and Immune Disorders, Cancer Research, 1990, pp. 1495-1502, vol. 50.

Kobayashi, Hisataka et al., Evaluation of the in Vivo Biodistribution of Indium-111 and Yttrium-88 Labeled Dendrimer-1B4M-DTPA and Its Conjugation with Anti-Tac Monoclonal Antibody, Bioconjugate Chemistry, 1999, pp. 103-111, vol. 10.

Kobayashi, Hisataka et al., Evaluation of the in Vivo Biodistribution of Yttrium-Labeled Isomers of CHX-DTPA-Conjugated Monoclonal Antibodies, Journal of Nuclear Medicine, 1998, pp. 829-836, vol. 39.

Kufer, Peter et al., A revival of bispecific antibodies, Trends in Biotechnology, 2004, pp. 238-244, vol. 22, No. 5.

(56) References Cited

OTHER PUBLICATIONS

Kukis, David L. et al., Optimized Conditions for Chelation of Yttrium-90-DOTA Immunoconjugates, Journal of Nuclear Medicine, 1998, pp. 2105-2110, vol. 39.
Lee, Fook-Thean et al., Specific Localization, Gamma Camera Imaging, and Intracellular Trafficking of Radiolabelled Chimeric Anti-GD3 Ganglioside Monoclonal Antibody KM871 in SK-MEL-28 Melanoma Xenografts, Cancer Research, 2001, pp. 4474-4482, vol. 61.
Lewis, Michael R. et al., An Improved Method for Conjugating Monoclonal Antibodies with N-Hydroxysulfosuccinimidyl DOTA, Bioconjugate Chemistry, 2001, pp. 320-324, vol. 12.
Li, Lin et al., Vinyl Sulfone Bifunctional Derivatives of DOTA Allow Sulfhydryl- or Amino-Directed Coupling to Antibodies. Conjugates Retain Immunoreactivity and Have Similar Biodistributions, Bioconjugate Chemistry, 2002, pp. 110-115, vol. 13.
Li, Wenkui et al., LC-MS/MS determination of a human mAb drug candidate in rat serum using an isotopically labeled universal mAb internal standard, Journal of Chromatography B, 2017, pp. 166-176, vol. 1044-1045.
MacCallum, Robert M. et al., Antibody-antigen Interactions: Contact Analysis and Binding Site Topography, Journal of Molecular Biology, 1996, pp. 732-745, vol. 262.
Means, Gary E. and Feeney, Robert E., Chemical Modifications of Proteins: History and Applications, Bioconjugate Chemistry, 1990, pp. 2-12, vol. 1.
Meares, C F. et al., Macrocyclic chelates of radiometals for diagnosis and therapy, British Journal of Cancer, 1990, pp. 21-26, vol. 62, Supp X.
Meares, Claude F. et al., Conjugation of Antibodies with Bifunctional Chelating Agents: Isothiocyanate and Bromoacetamide Reagents, Methods of Analysis, and Subsequent Addition of Metal Ions, Analytical Biochemistry, 1984, pp. 68-78, vol. 142.
Miederer, Matthias et al., Pharmacokinetics, Dosimetry, and Toxicity of the Targetable Atomic Generator, 225Ac-HuM195, in Nonhuman Primates, Journal of Nuclear Medicine, 2004, pp. 129-137, vol. 45.
Mier, Walter et al., Conjugation of DOTA Using Isolated Phenolic Active Esters: The Labeling and Biodistribution of Albumin as Blood Pool Marker, Bioconjugate Chemistry, 2005, pp. 237-240, vol. 16.
Mirzadeh, Saed et al., Radiometal Labeling of Immunoproteins: Covalent Linkage of 2-(4-Isothiocyanatobenzyl) diethylenetriaminepentaacetic Acid Ligands to Immunoglobulin, Bioconjugate Chemistry, 1990, pp. 59-65, vol. 1.
Mitchell, Paul et al., Targeting Primary Human Ph+ B-Cell Precursor Leukemia-Engrafted SCID Mice Using Radiolabeled Anti-CD19 Monoclonal Antibodies, Journal of Nuclear Medicine, 2003, pp. 1105-1112, vol. 44.
Nikula, Tuomo K. et al., A Rapid, Single Vessel Method for Preparation of Clinical Grade Ligand Conjugated Monoclonal Antibodies, Nuclear Medicine and Biology, 1995, pp. 387-390, vol. 22, No. 3.
Nikula, Tuomo K. et al., Alpha-Emitting Bismuth Cyclohexylbenzyl DTPA Constructs of Recombinant Humanized Anti-CD33 Antibodies: Pharmacokinetics, Bioactivity, Toxicity and Chemistry, Journal of Nuclear Medicine, 1999, pp. 166-176, vol. 40.
Noren, Christopher J. et al., A General Method for Site-Specific Incorporation of Unnatural Amino Acids into Proteins Science, 1989, pp. 182-188, vol. 244.

Pearson, William R. and Lipman, David J., "Improved tools for biological sequence comparison", Proceedings of the National Academy of Sciences USA, 1988, pp. 2444-2448, vol. 85.
Pearson, William R. et al., Comparison of DNA Sequences with Protein Sequences, Genomics, 1997, pp. 24-36, vol. 46, Article No. GE974995.
Pearson, William R., [15] Effective Protein Sequence Comparison, Methods in Enzymology, 1996, pp. 227-258, vol. 266.
Presta, Leonard G. et al., Humanization of an Anti-Vascular Endothelial Growth Factor Monoclonal Antibody for the Therapy of Solid Tumors and Other Disorders, Cancer Research, 1997, pp. 4593-4599, vol. 57.
Ramagiri, Suma, A Functionalized Assay—Hyphenating LBA with LC/MS: How far can we push to accomplish anything meaningful?, Sciex, 2015, EBF 8th Open Meeting, retrieved from http://bcn2015.europeanbioanalysisforum.eu/wp-content/uploads/2015/12/os-2015-D2A2_4-suma-Ramagirl.pdf, 42 pp.
Reineke, Ulrich, Antibody Epitope Mapping Using Arrays of Synthetic Peptides, Methods in Molecular Biology, Antibody Engineering Methods and Protocols, 2004, pp. 443-463, vol. 248.
Riechmann, Lutz et al., Uniform labeling of a recombinant antibody Fv-fragment with 15N and 13C for heteronuclear NMR spectroscopy, FEBS Letters, 1991, pp. 185-188, vol. 287, No. 1,2.
Roselli, Mario et al., In Vivo Comparison of CHX-DTPA Ligand Isomers in Athymic Mice Bearing Carcinoma Xernografts, Cancer Biotherapy & Radiopharmaceuticals, 1999, pp. 209-220, vol. 14, No. 3.
Roux, Aurélie et al., Applications of liquid chromatography coupled to mass spectrometry-based metabolomics in clinical chemistry and toxicology: A review, Clinical Biochemistry, 2011, pp. 119-135, vol. 44.
Roux, Kenneth H. et al., Comparisons of the Ability of Human IgG3 Hinge Mutants, IgM, IgE, and IgA2, to Form Small Immune Complexes: A Role for Flexibility and Geometry, Journal of Immunology, 1998, pp. 4083-4090, vol. 161.
Ruegg, Curtis L. et al., Improved in Vivo Stability and Tumor Targeting of Bismuth-labeled Antibody, Cancer Research, 1990, pp. 4221-4226, vol. 50.
Stadtman, Thressa C., Selenocysteine, Annual Reviews of Biochemistry, 1996, pp. 83-100, vol. 65.
Underdown, Brian J. and Schiff, J. Michael, Immunoglobulin A: Strategic Defense Initiative at the Mucosal Surface, Annual Review of Immunology, 1986, pp. 389-417, vol. 4.
Verel, Iris et al., Quantitative 89Zr Immuno-PET for In Vivo Scouting of 90Y-Labeled Monoclonal Antibodies in Xenograft-Bearing Nude Mice, Journal of Nuclear Medicine, 2003, pp. 1663-1670, vol. 44.
Vitetta, Ellen S. et al., Redesigning Nature's Poisons to Create Anti-Tumor Reagents, Science, 1987, pp. 1098-1104, vol. 238.
Camera et al.. Evaluation of a new DTPA-derivative chelator: comparative biodistribution and imaging studies of 111In-labeled B3 monoclonal antibody in athymic mice bearing human epidermoid carcinoma xenografts. Nuclear Medicine and Biology, 1994, pp. 955-962, Abstract only, vol. 21.
Mardirossian, et al.. The stability in liver homogenates of indium-111 and yttrium-90 attached to antibody via two popular chelators. Nuclear Medicine and Biology, 1993, pp. 65-74, vol. 20, No. 1.
Ong et al., A practical recipe for stable isotope labeling by amino acids in cell culture (SILAC), Nature Protocols, vol. 1, No. 6, Jan. 1, 2007, pp. 2650-2660.
Riechmann et al., Uniform labeling of a recombinant antibody Fv-fragment with 15N and 12C for heteronuclear NMR spectroscopy; FEBS 10015; Aug. 1991, vol. 287, No. 1 and 1, pp. 185-188.

\* cited by examiner

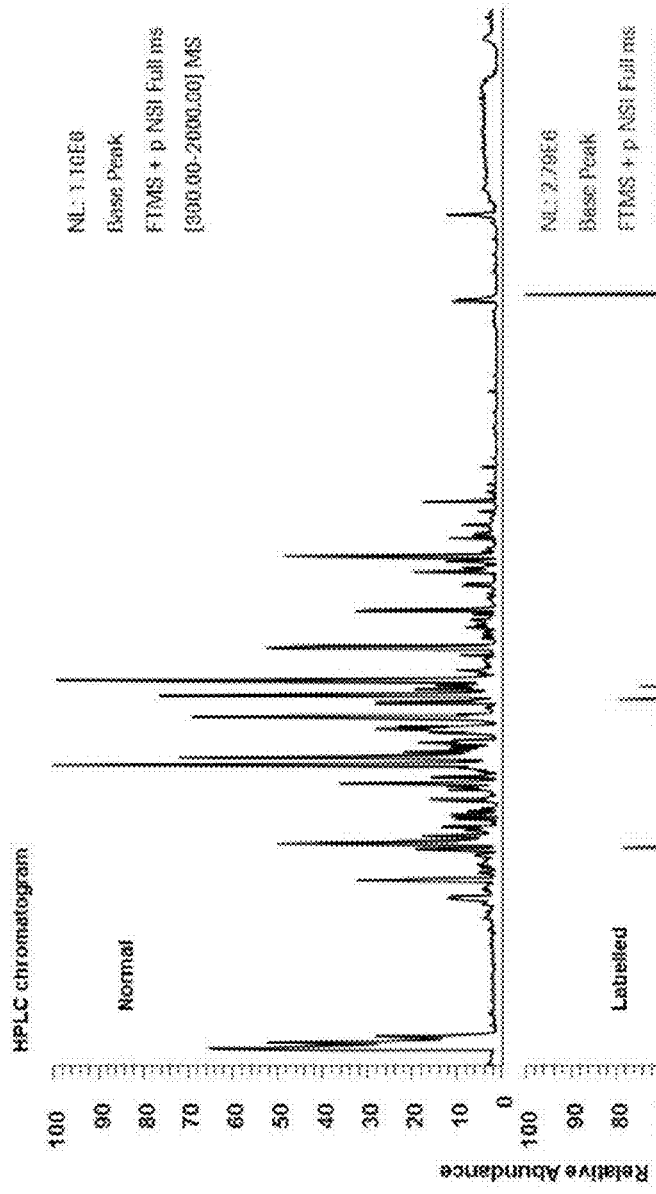
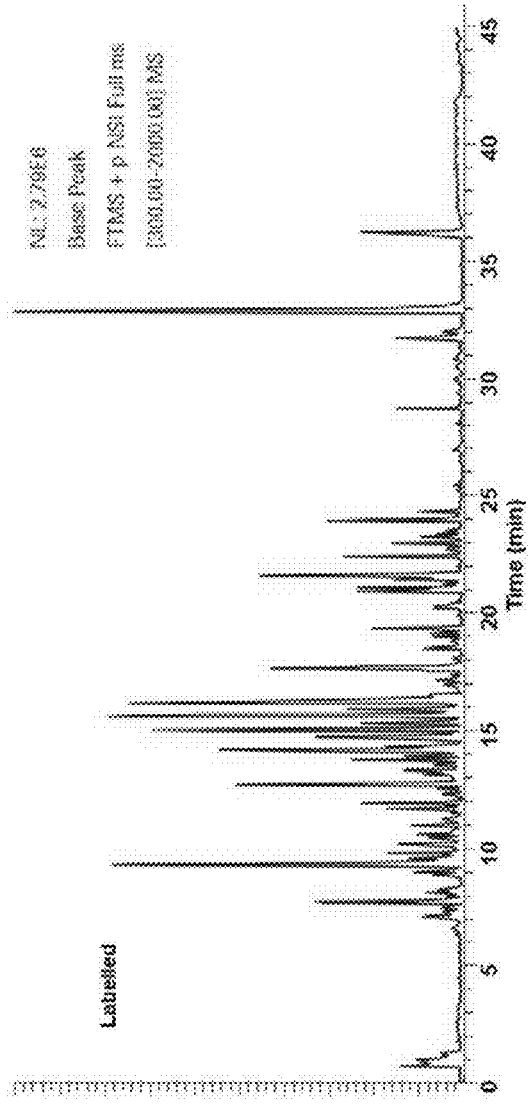
Fig. 1A
Fig. 1B

| antibody | RU | $k_a$ 1/Ms | $k_d$ 1/s | $t_{1/2}$-diss min | $K_D$ M | $K_D$ nM | $R_{max}$ RU | MR |
|---|---|---|---|---|---|---|---|---|
| M-11-7(C13) | 188 | 2,6E+06 | 2,6E-03 | 4 | 9,8E-10 | 1,0 | 73 | 1,6 |
| M-11-7(C13) | 221 | 2,3E+06 | 2,2E-03 | 5 | 9,5E-10 | 1,0 | 88 | 1,6 |
| M-11-7(C13) | 283 | 2,3E+06 | 2,3E-03 | 5 | 1,0E-09 | 1,0 | 108 | 1,5 |
| M-11-7 | 149 | 4,3E+05 | 1,0E-04 | 116 | 2,3E-10 | 0,2 | 60 | 1,6 |
| M-11-7 | 172 | 3,2E+05 | 1,3E-04 | 92 | 3,9E-10 | 0,4 | 77 | 1,8 |
| M-11-7 | 231 | 4,4E+05 | 1,1E-04 | 110 | 2,4E-10 | 0,2 | 91 | 1,6 |

Analyte:  2017/A01_rhcTNT_lyo

Temperature:  37°C

Ligands

2017/01_M-11-7(C13):

2017/02_M-11-7

SEQUENCE LISTING

<160> NUMBER OF SEQ ID NOS: 1

<210> SEQ ID NO 1
<211> LENGTH: 17
<212> TYPE: PRT
<213> ORGANISM: Artificial Sequence
<220> FEATURE:

```
<223> OTHER INFORMATION: Peptide of Antibody

<400> SEQUENCE: 1

Asn Thr Gln Pro Ile Met Asp Thr Asp Gly Ser Tyr Phe Val Tyr Ser
1               5                   10                  15

Lys
```

COPY PROTECTION FOR ANTIBODIES

CROSS-REFERENCE TO RELATED APPLICATION

This application is a continuation of International Application No. PCT/EP2018/078720 filed Oct. 19, 2018, which claims priority to European Application No. 17197603.8 filed Oct. 20, 2017, the disclosures of which are hereby incorporated by reference in their entirety.

FIELD OF THE INVENTION

The present invention is directed at an antibody conjugate comprising an antibody and a tag, wherein one or more element(s) present in the antibody exhibit an isotope ratio which differs from the naturally occurring isotope ratio of said one or more element(s), wherein the amount of the isotope which is less-common in nature, is increased to at least 4% of the atoms of the respective element in the antibody, as well as uses thereof.

BACKGROUND

The primary amino acid sequence of proteins, in particular of antibodies, including covalently linked modifications, may easily be determined using mass spectrometry (Applications of liquid chromatography coupled to mass spectrometry-based metabolomics in clinical chemistry and toxicology: A review, 2011, Volume: 44, Issue: 1, Pages: 119-135, Special Issue). Typically, the following steps are performed: a) the target is isolated; b) the target is digested enzymatically with a variety of different enzymes which generate a variety of peptides; c) the produced peptides are separated chromatographically; d) the mass of the intact peptides as well as their sequence-specific fragments is measured using mass spectrometry; e) software based interpretation of the measured data is used to identify the sequence of the peptides; e) the combination of overlapping peptides which were generated by the different proteases, is used to determine the complete amino acid sequence of the whole protein. For this process, only about 50 µg of the protein are required, as well as commercially available HPLC and Mass Spectrometry instrument (e.g. TripleTOF systems from ABSciex or Orbitrap based hybrid MS instrumentation from Thermofisher) and suitable software (e.g. PEAKS® Studio Software from Bioinformatics Solutions, Inc). So far no mechanism is available to protect proteins, such as antibodies, from being sequenced by mass spectrometry.

However, there is an urgent need in the art to protect proteins from being sequenced, in particular those proteins which may be of commercial interest in that they may be part of a pharmaceutical, diagnostic, and/or biotechnological product(s).

This problem is solved by the present inventors by providing proteins, in particular antibodies, which comprise an altered ratio of stable isotopes of one or more element(s), as well as methods of producing and using the same. The incorporation of an altered ratio of stable isotopes of one or more element(s) in a protein changes the mass of said protein. If analyzed using mass spectrometry, both, the mass of each of the generated peptides as well as the mass of the complete protein differs from those which occur naturally. Therefore, the determination of the sequence using available standard tools is not possible any more. A further advantage of the thus labeled protein, is the even distribution of isotopes within the protein which results in a decreased signal within the mass spectrometry spectrum.

SUMMARY OF THE INVENTION

In a first aspect, the present invention relates to an antibody conjugate comprising an antibody and a tag, wherein one or more element(s) present in the antibody exhibit an isotope ratio which differs from the naturally occurring isotope ratio of said one or more element(s), wherein the amount of the isotope which is less less-common in nature, is increased to at least 4% of the atoms of the respective element in the antibody. In a second aspect, the present invention relates to the use of an antibody conjugate as specified in the first aspect of the present invention, for preventing the sequencing of an antibody (in particular via Mass Spec).

In a third aspect, the present invention relates to the use of a stable isotopic label for protecting the sequence of an antibody conjugate as specified in the first aspect of the present invention from being determined (in particular via Mass Spec).

In a fourth aspect, the present invention relates to kit comprising at least one antibody conjugate as specified in the first aspect of the present invention.

LISTING OF FIGURES

FIG. 1A: Sequence coverage after LC-MS/MS, anti-TnT-antibody expressed in normal medium.

FIG. 1B: Sequence coverage after LC-MS/MS, anti-TnT-antibody expressed in C13 labeled medium.

FIG. 2: Simulation of isotopic effect.

Figure 3A:
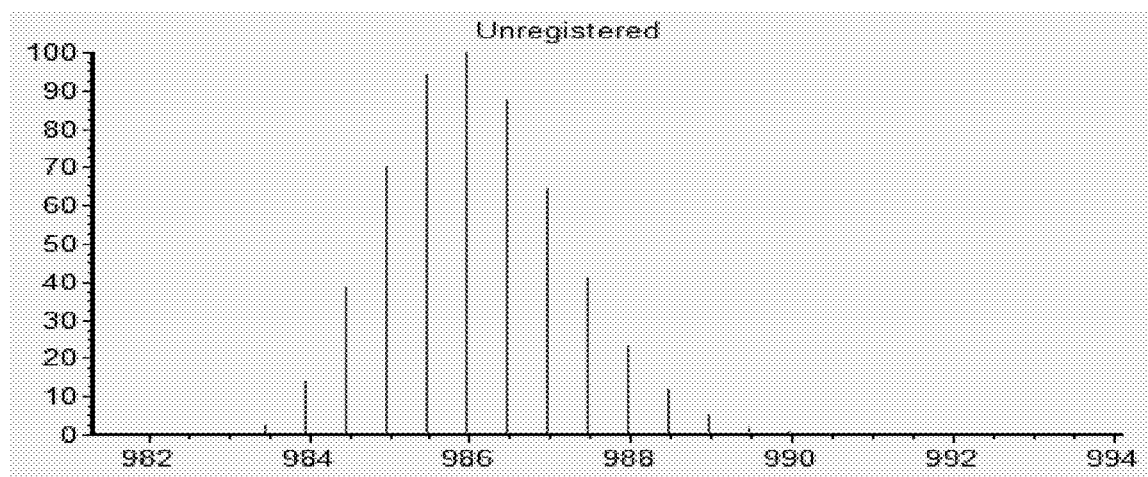

FIG. 3A: Measured spectra of Peptide NTQPIMDTDGSYFVYSK, simulation.

Figure 3B:
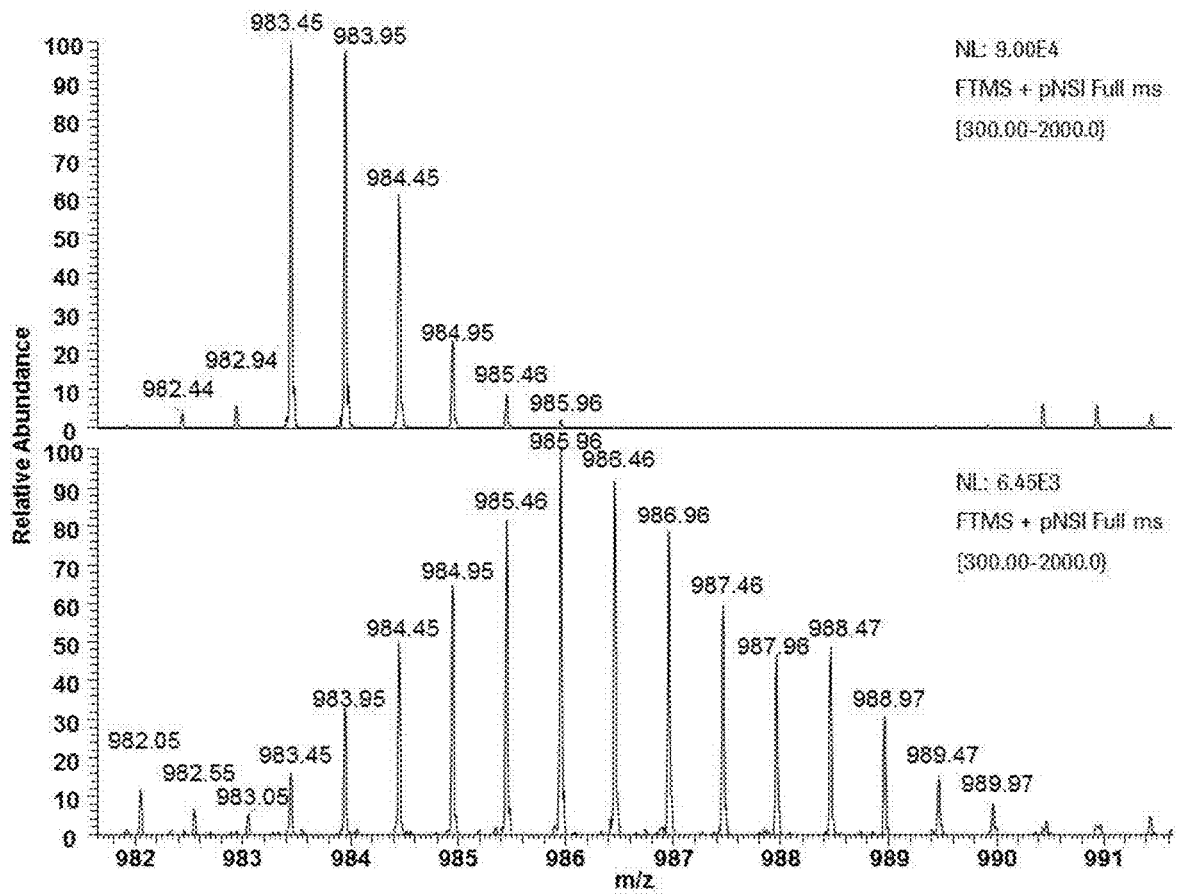

FIG. 3B: Measured spectra of Peptide NTQPIMDTDGSYFVYSK, anti-TnT-antibody expressed in normal (first spectrum) or C13 labeled medium (second spectrum).

Figure 4:
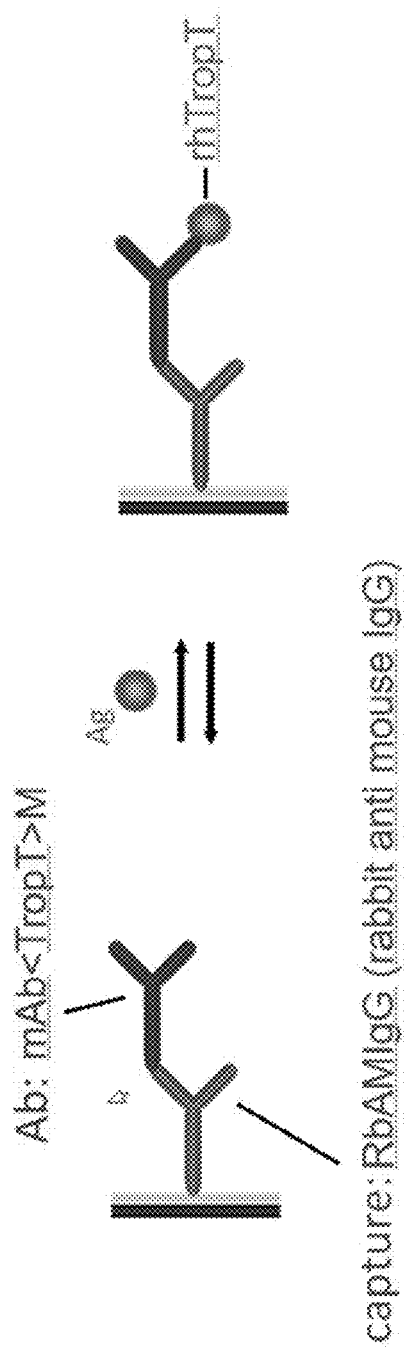

FIG. 4: Biacore Assay—Schematic Drawing.

Figures 5A, 5B:
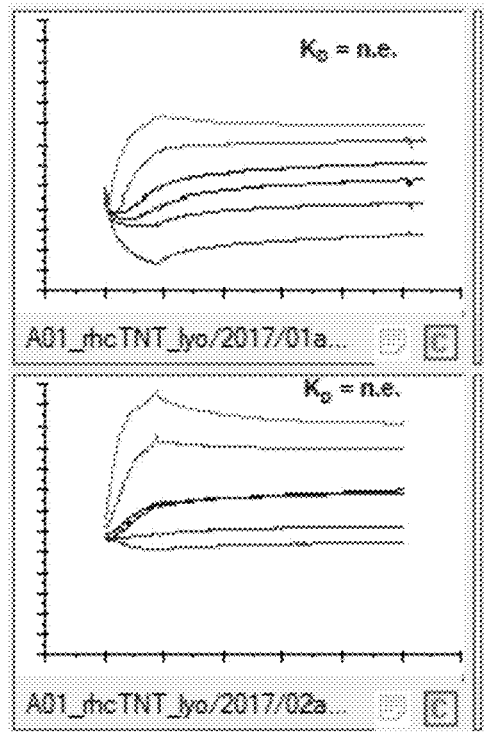

FIGS. 5A-B: Binding Affinity of anti-TnT-antibody in Biacore Assay.

DETAILED DESCRIPTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

The word "comprise", and variations such as "comprises" and "comprising", will be understood to imply the inclusion of a stated integer or step or group of integers or steps but not the exclusion of any other integer or step or group of integers or steps.

As used in this specification and the appended claims, the singular forms "a", "an", and "the" include plural referents, unless the content clearly dictates otherwise.

Percentages, concentrations, amounts, and other numerical data may be expressed or presented herein in a "range" format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "4 to 20%" should be interpreted to include not only the explicitly recited values of 4% to 20%, but to also include individual values and sub-ranges within the indicated range. Thus, included in this numerical range are individual values such as 4, 5, 6, 7, 8, 9, 10, . . . 18, 19, 20% and sub-ranges such as from 4-10%, 5-15%, 10-20%, etc. This same principle applies to ranges reciting only one numerical value, such as e.g. minimal or maximal values. Furthermore, such an interpretation should apply regardless of the breadth of the range or the characteristics being described.

The term "about" when used in connection with a numerical value is meant to encompass numerical values within a range having a lower limit that is 5% smaller than the indicated numerical value and having an upper limit that is 5% larger than the indicated numerical value.

The term "amino acid" generally refers to any monomer unit that comprises a substituted or unsubstituted amino group, a substituted or unsubstituted carboxy group, and one or more side chains or groups, or analogs of any of these groups. Exemplary side chains include, e.g., thiol, seleno, sulfonyl, alkyl, aryl, acyl, keto, azido, hydroxyl, hydrazine, cyano, halo, hydrazide, alkenyl, alkynl, ether, borate, boronate, phospho, phosphono, phosphine, heterocyclic, enone, imine, aldehyde, ester, thioacid, hydroxylamine, or any combination of these groups. Other representative amino acids include, but are not limited to, amino acids comprising photoactivatable cross-linkers, metal binding amino acids, spin-labeled amino acids, fluorescent amino acids, metal-containing amino acids, amino acids with novel functional groups, amino acids that covalently or noncovalently interact with other molecules, photocaged and/or photoisomerizable amino acids, radioactive amino acids, amino acids comprising biotin or a biotin analog, glycosylated amino acids, other carbohydrate modified amino acids, amino acids comprising polyethylene glycol or polyether, heavy atom substituted amino acids, chemically cleavable and/or photocleavable amino acids, carbon-linked sugar-containing amino acids, redox-active amino acids, amino thioacid containing amino acids, and amino acids comprising one or more toxic moieties. As used herein, the term "amino acid" includes the following twenty natural or genetically encoded alpha-amino acids: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). The term "non-essential" amino acid refers to those amino acids which can be synthesized by humans and are thus, not essential to the human diet. There are 11 non-essential amino acids: alanine, arginine, asparagine, aspartic acid, cysteine, glutamic acid, glutamine, glycine, proline, serine, and tyrosine. "Essential amino acids" are those which cannot be synthesized by the human body and thus, need to be provided by dietary protein. Essential amino acids include histidine, isoleucine, leucine, lysine, methionine, phenylalanine, threonine, tryptophan, valine. The structures of these twenty natural amino acids are shown in, e.g., Stryer et al., Biochemistry, 5th ed., Freeman and Company (2002). Additional amino acids, such as selenocysteine and pyrrolysine, can also be genetically coded for (Stadtman (1996) "Selenocysteine," Annu Rev Biochem. 65:83-100 and Ibba et al. (2002) "Genetic code: introducing pyrrolysine," Curr Biol. 12(13):R464-R466). The term "amino acid" also includes unnatural amino acids, modified amino acids (e.g., having modified side chains and/or backbones), and amino acid analogs. Amino acids can be merged into peptides, polypeptides, or proteins.

In the context of the present invention, the term "peptide" refers to a short polymer of amino acids linked by peptide bonds. It has the same chemical (peptide) bonds as proteins, but is commonly shorter in length. The shortest peptide is a dipeptide, consisting of two amino acids joined by a single peptide bond. There can also be a tripeptide, tetrapeptide, pentapeptide, etc. Typically, a peptide has a length of up to 4, 6, 8, 10, 12, 15, 18 or 20 amino acids. A peptide has an amino end and a carboxyl end, unless it is a cyclic peptide.

In the context of the present invention, the term "polypeptide" refers to a single linear chain of amino acids bonded together by peptide bonds and typically comprises at least about 21 amino acids, i.e. at least 21, 22, 23, 24, 25, etc. amino acids. A polypeptide can be one chain of a protein that is composed of more than one chain or it can be the protein itself if the protein is composed of one chain.

In the context of the different aspects of present invention, the term "protein" refers to a molecule comprising one or more polypeptides that resume a secondary and tertiary structure and additionally refers to a protein that is made up of several polypeptides, i.e. several subunits, forming quaternary structures. The protein has sometimes non-peptide groups attached, which can be called prosthetic groups or cofactors.

As used herein, the term "variant" is to be understood as a molecule which differs in comparison to the molecule from which it is derived by one or more changes in its length or sequence. The molecule from which the variant is derived, is also known as the parent molecule. The term "variant"

comprises "fragments" or "derivatives" of the parent molecule. Typically, "fragments" are smaller in length or size than the parent molecule, whilst "derivatives" exhibit one or more differences in their sequence in comparison to the parent molecule. Also encompassed are modified molecules such as but not limited to post-translationally modified proteins (e.g. glycosylated, biotinylated, phosphorylated, ubiquitinated, palmitoylated, or proteolytically cleaved proteins) and modified nucleic acids such as methylated DNA. Also mixtures of different molecules such as but not limited to RNA-DNA hybrids, are encompassed by the term "variant". Typically, a variant is constructed artificially, preferably by gene-technological means, whilst the parent protein or polynucleotide is a wild-type protein or polynucleotide, or a consensus sequence thereof. However, also naturally occurring variants are to be understood to be encompassed by the term "variant" as used herein. Further, the variants usable in the present invention may also be derived from homologs, orthologs, or paralogs of the parent molecule or from artificially constructed variant, provided that the variant exhibits at least one biological activity of the parent molecule, i.e. is functionally active.

In particular, the terms "peptide variant", "polypeptide variant", "protein variant" are to be understood as a peptide, polypeptide, or protein which differs in comparison to the peptide, polypeptide, or protein from which it is derived by one or more changes in the amino acid sequence. The peptide, polypeptide, or protein, from which the respective variant is derived, is also known as the parent peptide, polypeptide, or protein. Further, the variants usable in the present invention may also be derived from homologs, orthologs, or paralogs of the parent peptide, polypeptide, or protein or from artificially constructed variant, provided that the variant exhibits at least one biological activity of the parent peptide, polypeptide, or protein. The changes in the amino acid sequence may be amino acid exchanges, insertions, deletions, N-terminal truncations, or C-terminal truncations, or any combination of these changes, which may occur at one or several sites. A polypeptide or protein variant may exhibit a total number of up to 200 (up to 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200) changes in the amino acid sequence (i.e. exchanges, insertions, deletions, N-terminal truncations, and/or C-terminal truncations). The amino acid exchanges may be conservative and/or non-conservative. Alternatively or additionally, a "variant" as used herein, can be characterized by a certain degree of sequence identity to the parent peptide, polypeptide, or protein from which it is derived. More precisely, a peptide, polypeptide, or protein variant in the context of the present invention exhibits at least 80% sequence identity to its parent peptide, polypeptide, or protein. The sequence identity of polypeptide or protein variants is over a continuous stretch of 20, 30, 40, 50, 60, 70, 80, 90, 100 or more amino acids.

"Percent (%) amino acid sequence identity" with respect to a reference sequence is defined as the percentage of amino acid residues in a candidate sequence that are identical with the amino acid residues in the reference parent sequence, after aligning the sequences and introducing gaps, if necessary, to achieve the maximum percent sequence identity, and not considering any conservative substitutions as part of the sequence identity for the purposes of the alignment. Alignment for purposes of determining percent amino acid sequence identity can be achieved in various ways that are within the skill in the art, for instance, using publicly available computer software such as BLAST, BLAST-2, Clustal W, Megalign (DNASTAR) software or the FASTA program package. The FASTA program package was authored by W. R. Pearson and D. J. Lipman (1988), "Improved Tools for Biological Sequence Analysis", PNAS 85:2444-2448; W. R. Pearson (1996) "Effective protein sequence comparison" Meth. Enzymol. 266:227-258; and Pearson et. al. (1997) Genomics 46:24-36 and is publicly available from http://www.ebi.ac.uk/Tools/sss/fasta/ Those skilled in the art can determine appropriate parameters for aligning sequences, including any algorithms needed to achieve maximal alignment over the full length of the sequences being compared.

The term "amino acid mutation" or "amino acid alteration" denotes a modification in the amino acid sequence of a parent amino acid sequence. Exemplary modifications include amino acid substitutions, insertions, and/or deletions.

The term "amino acid mutations at the position" or "amino acid alteration at the position" denotes the substitution or deletion of the specified residue, or the insertion of at least one amino acid residue adjacent the specified residue. The term "insertion adjacent to a specified residue" denotes the insertion within one to two residues thereof. The insertion may be N-terminal or C-terminal to the specified residue.

The term "amino acid substitution" denotes the replacement of at least one amino acid residue in a predetermined parent amino acid sequence with a different "replacement" amino acid residue. The replacement residue or residues may be a "naturally occurring amino acid residue" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). The amino acid exchanges may be conservative, semi-conservative and/or non-conservative. Semi-conservative and especially conservative amino acid substitutions, wherein an amino acid is substituted with a chemically related amino acid are preferred. Typical substitutions are among the aliphatic amino acids, among the amino acids having aliphatic hydroxyl side chain, among the amino acids having acidic residues, among the amide derivatives, among the amino acids with basic residues, or the amino acids having aromatic residues. Typical semi-conservative and conservative substitutions are:

| Amino acid | Conservative substitution | Semi-conservative substitution |
|---|---|---|
| A | G; S; T | N; V; C |
| C | A; V; L | M; I; F; G |
| D | E; N; Q | A; S; T; K; R; H |
| E | D; Q; N | A; S; T; K; R; H |
| F | W; Y; L; M; H | I; V; A |
| G | A | S; N; T; D; E; N; Q |
| H | Y; F; K; R | L; M; A |
| I | V; L; M; A | F; Y; W; G |
| K | R; H | D; E; N; Q; S; T; A |
| L | M; I; V; A | F; Y; W; H; C |
| M | L; I; V; A | F; Y; W; C; |
| N | Q | D; E; S; T; A; G; K; R |
| P | V; I | L; A; M; W; Y; S; T; C; F |
| Q | N | D; E; A; S; T; L; M; K; R |
| R | K; H | N; Q; S; T; D; E; A |
| S | A; T; G; N | D; E; R; K |
| T | A; S; G; N; V | D; E; R; K; I |

-continued

| Amino acid | Conservative substitution | Semi-conservative substitution |
|---|---|---|
| V | A; L; I | M; T; C; N |
| W | F; Y; H | L; M; I; V; C |
| Y | F; W; H | L; M; I; V; C |

Changing from A, F, H, I, L, M, P, V, W or Y to C is semi-conservative if the new cysteine remains as a free thiol. Furthermore, the skilled person will appreciate that glycines at sterically demanding positions should not be substituted and that P should not be introduced into parts of the protein which have an alpha-helical or a beta-sheet structure.

Substitution with one or more non-naturally occurring amino acid residues is also encompassed by the definition of an amino acid substitution herein. A "non-naturally occurring amino acid residue" denotes a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine, α-Aminoisobutyric acid (Aib) and other amino acid residue analogues such as those described in Ellman, et al., Meth. Enzym. 202 (1991) 301-336. To generate such non-naturally occurring amino acid residues, the procedures of Noren, et al. (Science 244 (1989) 182) and/or Ellman, et al. (supra) can be used. Briefly, these procedures involve chemically activating a suppressor tRNA with a non-naturally occurring amino acid residue followed by in vitro transcription and translation of the RNA.

The term "amino acid deletion" denotes the removal of at least one amino acid residue at a predetermined position in an amino acid sequence.

Within this application whenever an amino acid alteration is mentioned it is a deliberated amino acid alteration and not a random amino acid modification.

The term "antigen" refers to any substance that causes an immune system to produce antibodies against it. An antigen may originate from within the body ("self-antigen") or from the external environment ("non-self"). Antigen presenting cells present antigens in the form of peptides on histocompatibility molecules. The T cells of the adaptive immune system recognize the antigens. Depending on the antigen and the type of the histocompatibility molecule, different types of T cells are activated.

An "epitope", also known as "antigenic determinant", is the segment of a macromolecule, in particular a segment of an antigen, either proteinaceous or non-proteinaceous, which is recognized by the immune system, specifically by antibodies, B cells, or T cells. An epitope is typically part of an antigen and is capable of being bound by an antibody or antigen-binding fragment thereof. In this context, the term "binding" preferably relates to a specific binding. In the context of the present invention the term "epitope" refers to the segment of protein that is recognized by an antibody. Epitopes usually consist of chemically active surface groupings of molecules such as amino acids or sugar side chains and usually have specific three-dimensional structural characteristics, as well as specific charge characteristics. Conformational and non-conformational epitopes are distinguished in that the binding to the former but not the latter is lost in the presence of denaturing solvents. Screening for antibodies binding to a particular epitope (i.e., those binding to the same epitope) can be done using methods routine in the art such as, e.g., without limitation, alanine scanning, peptide blots (see Meth. Mol. Biol. 248 (2004) 443-463), peptide cleavage analysis, epitope excision, epitope extraction, chemical modification of antigens (see Prot. Sci. 9 (2000) 487-496), and cross-blocking (see "Antibodies," Harlow and Lane (Cold Spring Harbor Press, Cold Spring Harb., N.Y.). Antigen Structure-based Antibody Profiling (ASAP), also known as Modification-Assisted Profiling (MAP), allows to bin a multitude of monoclonal antibodies specifically binding to a certain antigen based on the binding profile of each of the antibody antibodies from the multitude to chemically or enzymatically modified antigen surfaces (see, e.g., US 2004/0101920). The antibodies in each bin bind to the same epitope which may be a unique epitope either distinctly different from or partially overlapping with epitope represented by another bin. Also competitive binding can be used to easily determine whether an antibody binds to the same epitope of an antigen as, or competes for binding with, a reference antibody to the same antigen. embodiments two antibodies are deemed to bind to the same or an overlapping epitope if a 1-, 5-, 10-, 20- or 100-fold excess of one antibody inhibits binding of the other by at least 50%, at least 75%, at least 90% or even 99% or more as measured in a competitive binding assay (see, e.g., Junghans et al., Cancer Res. 50 (1990) 1495-1502).

In some embodiments two antibodies are deemed to bind to the same epitope if essentially all amino acid mutations in the antigen that reduce or eliminate binding of one antibody also reduce or eliminate binding of the other. Two antibodies are deemed to have "overlapping epitopes" if only a subset of the amino acid mutations that reduce or eliminate binding of one antibody reduce or eliminate binding of the other.

The term "antibody" as used herein refers to secreted immunoglobulins (Ig) which lack the transmembrane region and can thus, be released into the bloodstream and body cavities. "Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded.

Human antibodies are grouped into different isotypes based on the heavy chain they possess. There are five types of human Ig heavy chains denoted by the Greek letters: α, γ, δ, ε, and μ. The type of heavy chain present defines the class of antibody each performing different roles, and directing the appropriate immune response against different types of antigens. Accordingly, the "class" of an antibody refers to the type of constant domain or constant region possessed by its heavy chain. The five major classes of antibodies are: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$.

Distinct heavy chains differ in size and composition; and may comprise approximately 450 amino acids (Janeway et al. (2001) Immunobiology, Garland Science). IgA is found in mucosal areas, such as the gut, respiratory tract and urogenital tract, as well as in saliva, tears, and breast milk and prevents colonization by pathogens (Underdown & Schiff (1986) Annu. Rev. Immunol. 4:389-417). IgD mainly functions as an antigen receptor on B cells that have not been exposed to antigens and is involved in activating basophils and mast cells to produce antimicrobial factors (Geisberger et al. (2006) Immunology 118:429-437; Chen et al. (2009) Nat. Immunol. 10:889-898). IgE is involved in allergic reactions via its binding to allergens triggering the release of histamine from mast cells and basophils. IgE is also involved in protecting against parasitic worms (Pier et al.

(2004) Immunology, Infection, and Immunity, ASM Press). IgG provides the majority of antibody-based immunity against invading pathogens and is the only antibody isotype capable of crossing the placenta to give passive immunity to fetus (Pier et al. (2004) Immunology, Infection, and Immunity, ASM Press). In humans there are four different IgG subclasses (IgG1, 2, 3, and 4), named in order of their abundance in serum with IgG1 being the most abundant (~66%), followed by IgG2 (~23%), IgG3 (~7%) and IgG (~4%). The biological profile of the different IgG classes is determined by the structure of the respective hinge region. IgM is expressed on the surface of B cells in a monomeric form and in a secreted pentameric form with very high avidity. IgM is involved in eliminating pathogens in the early stages of B cell mediated (humoral) immunity before sufficient IgG is produced (Geisberger et al. (2006) Immunology 118:429-437). Antibodies are not only found as monomers but are also known to form dimers of two Ig units (e.g. IgA), tetramers of four Ig units (e.g. IgM of teleost fish), or pentamers of five Ig units (e.g. mammalian IgM). Antibodies are typically made of four polypeptide chains comprising two identical heavy chains and identical two light chains which are connected via disulfide bonds and resemble a "Y"-shaped macro-molecule. Each of the chains comprises a number of immunoglobulin domains out of which some are constant domains and others are variable domains. Immunoglobulin domains consist of a 2-layer sandwich of between 7 and 9 antiparallel strands arranged in two β-sheets.

Typically, the "heavy chain" of an antibody comprises four Ig domains with three of them being "constant domains" (CH domains: CH1, CH2, CH3) and one of them being a "variable domain" (VH domain). The "light chain" typically comprises one constant Ig domain (CL) and one variable Ig domain (VL). Exemplified, the human IgG heavy chain is composed of four Ig domains linked from N- to C-terminus in the order CH1-CH2-CH3, whereas the human IgG light chain is composed of two immunoglobulin domains linked from N- to C-terminus in the order VL-CL, being either of the kappa or lambda type ($V_\kappa$—$C_\kappa$ or Vλ-Cλ). Exemplified, the constant chain of human IgG comprises 447 amino acids.

Accordingly, the term "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites. The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called "hypervariable regions" (HVRs) both in the light-chain and the heavy-chain variable domains. The more highly conserved portions of variable domains are called the "framework regions" (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., Sequences of Proteins of Immunological Interest, Fifth Edition, National Institute of Health, Bethesda, Md. (1991)). Accordingly, the term "hypervariable region" or "HVR" as used herein refers to each of the regions of an antibody variable domain which are hypervariable in sequence (also called "complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., supra);

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

The "Framework region" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "position" denotes the location of an amino acid residue in the amino acid sequence of a peptide chain. Positions may be numbered sequentially, or according to an established format, for example the "EU index of Kabat" for antibody numbering (Kabat, E. A., Wu, T. T., Perry, H. M., Gottesman, K. S., and Foeller, C., Sequences of Proteins of Immunological Interest, 5th ed., Public Health Service, National Institutes of Health, Bethesda, Md. (1991), NIH Publication 91-3242, expressly incorporated herein by reference). The "EU index as in Kabat" refers to the residue numbering of the human IgG 1EU antibody. Accordingly, CH domains in the context of IgG are as follows: "CH1" refers to amino acid positions 118-220 according to the EU index as in Kabat; "CH2" refers to amino acid positions 237-340 according to the EU index as in Kabat; and "CH3" refers to amino acid positions 341-447 according to the EU index as in Kabat. Unless otherwise indicated, HVR (e.g. CDR) residues and other residues in the variable domain (e.g. FR residues) are numbered herein according to Kabat et al., supra.

The constant domains are not directly involved in the binding of an antibody to an antigen, but exhibit various effector functions. The "effector functions" refer to those biological activities attributable to the constant domains of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "hinge region" denotes the part of an antibody heavy chain polypeptide that joins in a wild-type antibody heavy chain the CH1 domain and the CH2 domain, e. g. for human IgG1 from about position 216 to about position 238 according to the EU number system (http://www.imgt.org/IMGTScientificChart/Numbering/Hu_IGHGnber.html), or from about position 226 to about position 243 of Kabat numbering. Position 226 according to Kabat corresponds to position 99 of a human IgG1 heavy chain constant region. The hinge regions of other IgG subclasses can be determined by aligning with the hinge-region cysteine residues of the human IgG1 subclass sequence. The hinge region is normally dimeric consisting of two polypeptides with identical amino acid sequence. The hinge region generally comprises about 25 amino acid residues and is flexible allowing the antigen binding regions to move independently. The hinge region can be subdivided into three domains: the upper, the middle, and the lower hinge domain (see e.g. Roux, et al., J. Immunol. 161 (1998) 4083). The term "upper hinge region" of an Fc-region, e. g. for human IgG1, denotes the stretch of amino acid residues N-terminal to the middle hinge region, i.e. residues 216 to 225 of the Fc-region according to the EU numbering. The term "middle hinge region", e. g. for human IgG1, i.e. residues 226 to 230 of the Fc-region according to the EU numbering, denotes the stretch of amino acid residues comprising the cross-linking cysteine residues, is rich in prolines and cysteines, and it is located between the upper and the lower hinge region. The term "lower hinge region" of an Fc-region, e. g. for human IgG1, denotes the stretch of amino acid residues immediately C-terminal to the middle hinge region, i.e. residues 231 to 238 of the Fc-region according to the EU numbering.

The term "antibody" encompasses monoclonal antibodies, polyclonal antibodies, multispecific antibodies (e.g., bispecific antibodies), and antibody fragments so long as they exhibit the desired antigen-binding activity. The term encompasses both, full-length antibodies as well as fragments thereof. The terms "full-length antibody" "intact antibody" and "whole antibody" are used herein interchangeably to refer to an antibody in its substantially intact form, but not to antibody fragments as defined below. The term thus denotes an antibody that has a structure and amino acid sequence substantially identical to a native antibody.

The term "chimeric" antibody refers to an antibody in which a portion of the heavy and/or light chain is derived from a particular source or species, while the remainder of the heavy and/or light chain is derived from a different source or species.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) methods. For a review of methods for assessment of antibody purity, see, e.g., Flatman et al., J. Chromatogr. B 848:79-87 (2007).

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a tag.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). An "affinity matured" antibody refers to an antibody with one or more alterations in one or more hypervariable regions (HVRs), compared to a parent antibody which does not possess such alterations, such alterations resulting in an improvement in the affinity of the antibody for antigen. Affinity can be measured by common methods known in the art, including those described herein. Specific illustrative and exemplary embodiments for measuring binding affinity are described in the following: Exemplified, the Kd may be measured using a BIACORE® surface plasmon resonance assay. A BIACORE®-2000 or a BIACORE®-3000 (BIAcore, Inc., Piscataway, N.J.) assay is performed at 37° C. with immobilized antigen CM5 chips at ~10 response units (RU). Carboxymethylated dextran biosensor chips (CM5, BIACORE, Inc.) may be activated with N-ethyl-N'-(3-dimethylaminopropyl)-carbodiimide hydrochloride (EDC) and N-hydroxysuccinimide (NHS) according to the supplier's instructions. Antigen may be diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine injection blocks unreacted groups. For kinetics measurements, two-fold serial dilutions of Fab (0.78 nM to 500 nM) are injected in PBS with 0.05% polysorbate 20 (TWEEN-20™) surfactant (PBST) and optionally 5% DMSO at 37° C. at a flow rate of approximately 25 µl/min. Association rates (kon) and dissociation rates (koff) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio koff/kon. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 37° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

In an alternative method, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

Papain digestion of antibodies produces two identical antigen binding fragments, called "Fab fragments" (also referred to as "Fab portion" or "Fab region") each with a single antigen binding site, and a residual "Fc fragment" (also referred to as "Fc portion" or "Fc region") whose name reflects its ability to crystallize readily. The crystal structure of the human IgG Fc region has been determined in the 1980s. In IgG, IgA and IgD isotypes, the Fc region is composed of two identical protein fragments, derived from the CH2 and CH3 domains of the antibody's two heavy chains; in IgM and IgE isotypes, the Fc regions contain three heavy chain constant domains (CH2-4) in each polypeptide chain. In addition, smaller immunoglobulin molecules exist naturally or have been constructed artificially.

The term "Fab' fragment" refers to a Fab fragment additionally comprise the hinge region of an Ig molecule whilst "F(ab')2 fragments" are understood to comprise two Fab' fragments being either chemically linked or connected via a disulfide bond.

Whilst "single domain antibodies (sdAb)" (Desmyter et al. (1996) Nat. Structure Biol. 3:803-811) and "Nanobodies" only comprise a single VH domain, "single chain Fv (scFv)" fragments comprise the heavy chain variable domain joined via a short linker peptide to the light chain variable domain (Huston et al. (1988) Proc. Natl. Acad. Sci. USA 85, 5879-5883). Divalent single-chain variable fragments (di-scFvs) can be engineered by linking two scFvs (scFvA-scFvB). This can be done by producing a single peptide chain with two VH and two VL regions, yielding "tandem scFvs" (VHA-VLA-VHB-VLB). Another possibility is the creation of scFvs with linkers that are too short for the two variable regions to fold together, forcing scFvs to dimerize. Usually linkers with a length of 5 residues are used to generate these dimers. This type is known as "diabodies". Still shorter linkers (one or two amino acids) between a VH and VL domain lead to the formation of monospecific trimers, so-called "triabodies" or "tribadies". Bispecific diabodies are formed by expressing to chains with the arrangement VHA-VLB and VHB-VLA or VLA-VHB and VLB-VHA, respectively. Single chain diabodies (scDb) comprise a VHA-VLB and a VHB-VLA fragment which are linked by a linker peptide (P) of 12-20 amino acids, preferably 14 amino acids, (VHA-VLB-P-VHB-VLA). "Bi-specific T-cell engagers (BiTEs)" are fusion proteins consisting of two scFvs of different antibodies wherein one of the scFvs binds to T cells via the CD3 receptor, and the other to a tumor cell via a tumor specific molecule (Kufer et al. (2004) Trends Biotechnol. 22:238-244). Dual affinity retargeting molecules ("DART" molecules) are diabodies additionally stabilized through a C-terminal disulfide bridge.

Accordingly, the term "antibody fragments" refers to a portion of an intact antibody, preferably comprising the antigen-binding region thereof. Antibody fragments include but are not limited to Fab, Fab', F(ab')$_2$, Fv fragments; diabodies; triabodies, sdAb, nanobodies, scFv, di-scFvs, tandem scFvs, scDb, BiTEs, and DARTs.

The term "conjugate" as used herein, refers to a whole that comprehends a number of individual components, parts or moieties which are in close proximity to each other and fulfil a common or interrelated function. The individual moieties of a conjugate may be of the same or of differing nature, i.e. they may be composed of the same, a similar or of differing chemical entity such as but not limited to nucleotides, amino acids, nucleic acids, peptides, polypeptides, proteins, carbohydrates, or lipids. Exemplified, a conjugate may comprise a number of associated peptides, polypeptides, or proteins, or a mixture of proteins and one or more nucleic acids or a mixture of one or more proteins and one or more lipids and/or carbohydrates. It is understood that any other combination of identical, similar or differing chemical entities is also encompassed. The individual moieties of a conjugate may or may not be interconnected. Typically, the individual parts of a conjugate are connected via covalent or non-covalent bonds. The term "antibody conjugate" refers to a conjugate comprising an antibody and one or more additional moieties, including but not limited to a label and/or a tag.

In the context of the present disclosure, a "tag" refers to a moiety which is attached to the protein. A tag may be attached to a protein to allow for the protein to be detected or may be attached to said protein to provide the protein with a specific function. Suitable detectable tags include but are not limited to fluorescent dye (e.g. GFT and its variants, FITC, TRITC, fluorescein and rhodamine, and the like), electron-dense reagents (e.g. gold), enzymes (e.g. as commonly used in an ELISA), chemiluminescent molecules, electrochemiluminescent molecules, biotin, digoxigenin, or hapten and other entities which are detectable or can be made detectable. Exemplified, an antibody may be biotinylated or ruthenylated. Tags providing a protein with a specific function include but are not limited to partner of a binding pair, a functional group, a therapeutic agent (drug) and/or a cytotoxic agent (e.g. a toxin such as doxorubicin or pertussis toxin).

Methods for attaching a tag to an antibody are well-known to the person skilled in the art and abundantly described e.g. in Haugland (2003) Molecular Probes Handbook of Fluorescent Probes and Research Chemicals, Molecular Probes, Inc.; Brinkley (1992) Bioconjugate Chem. 3:2; Garman, (1997) Non-Radioactive Labeling: A Practical Approach, Academic Press, London; Means (1990) Bioconjugate Chem. 1:2; Glazer et al Chemical Modification of Proteins. Laboratory Techniques in Biochemistry and Molecular Biology (T. S. Work and E. Work, Eds.) American Elsevier Publishing Co., New York; Lundblad, R. L. and Noyes, C. M. (1984) Chemical Reagents for Protein Modification, Vols. I and II, CRC Press, New York; Pfleiderer, G. (1985) "Chemical Modification of Proteins", Modern Methods in Protein Chemistry, H. Tschesche, Ed., Walter DeGruyter, Berlin and New York; and Wong (1991) Chemistry of Protein Conjugation and Cross-linking, CRC Press, Boca Raton, Fla.); DeLeon-Rodriguez et al, Chem. Eur. J. 10 (2004) 1149-1155; Lewis et al, Bioconjugate Chem. 12 (2001) 320-324; Li et al, Bioconjugate Chem. 13 (2002) 110-115; Mier et al Bioconjugate Chem. 16 (2005) 240-237.

Label

In the context of the present disclosure, a "label" refers to molecules which have an altered structure, in a manner to be detectable themselves without an additional tag being attached. Examples of such label include but are not limited to radioisotopes or stable isotopic label.

Isotopes are variants of a particular chemical element which differ in the number of neutron. All isotopes of a given element have the same number of protons in each atom. The number of protons within the atom's nucleus is called atomic number and is equal to the number of electrons in the neutral (non-ionized) atom. Each atomic number identifies a specific element, but not the isotope; an atom of a given element may have a wide range in its number of neutrons. The number of nucleons (both protons and neutrons) in the nucleus is the atom's mass number, and each isotope of a given element has a different mass number. For example, carbon-12 ($^{12}C$), carbon-13 ($^{13}C$), and carbon-14 ($^{14}C$) are three isotopes of the element carbon with mass numbers 12, 13, and 14, respectively. The atomic number of carbon is 6, which means that every carbon atom has 6 protons, so that the neutron numbers of these isotopes are 6, 7 and 8, respectively. Some isotopes are radioactive, and are thus referred to as "radioisotopes" or "unstable isotope", whereas others have never been observed to decay radioactively and are referred to as "stable isotopes". For example, $^{14}C$ is a radioisotope of carbon, whereas $^{12}C$ and $^{13}C$ are stable isotopes. 98.9% of carbon occurring in nature is $^{12}C$ (also referred to as the "common isotope"), whereas only 1.1% are $^{13}C$ (also referred to as the "less-common isotope"). A further example is nitrogen (N) which consists of two stable isotopes, nitrogen-14, which makes up the vast majority of naturally occurring nitrogen ($^{14}N$: 99.6%, the common isotope), and nitrogen-15 ($^{15}N$: 0.4%, the less-common isotope). There are even three stable isotopes of oxygen (O): $^{16}O$, $^{17}O$, and $^{18}O$, with a natural distribution of 99.76% (the common isotope), 0.04% (less-common isotope), and 0.20% (less-common isotope), respectively. Also Hydrogen (H) has three naturally occurring isotopes, sometimes denoted $^{1}H$ (also called protium), $^{2}H$ (also called deuterium), and $^{3}H$ (also called tritium), with the first two being stable and the third one having a half-life of 12.32 years. 99.98% percent of naturally occurring H is $^{1}H$ (the common isotope), whereas only 0.02% of naturally occurring H are $^{2}H$ (the less-common isotope).

Accordingly, the term "common isotope" refers to the isotope of an atom which makes up the vast majority of naturally occurring isotopes. Exemplified, the common stable isotope of carbon is $^{12}C$. The common stable isotope of nitrogen is $^{14}N$. The common stable isotope of oxygen is $^{16}O$, and the common stable isotope of hydrogen is $^{1}H$.

Accordingly, the term "less-common isotope" refers to the isotope of an atom which makes up the minority of naturally occurring isotopes. Exemplified, the less-common stable isotope of carbon is $^{13}C$. The less-common stable isotope of nitrogen is $^{15}N$. The less-common stable isotope of oxygen is $^{17}O$ or $^{18}O$, and the less-common stable isotope of hydrogen is $^{2}H$.

The term "ratio" refers to the relationship between two numerical values. In the context of the present disclosure the term "ratio" in particular refers to the relationship between the percentage of isotopes of a given element in a protein. The term "altered ratio" relates to the isotope distribution of a certain elements which is different from the natural isotope distribution. Exemplified, an altered ratio of carbon isotopes is present in case more than 1.1% $^{13}C$ atoms are present in a protein, e.g. if 5%, 10% or 20% of carbon present in a protein are $^{13}C$. In such case the isotope distribution is altered from 98.9% $^{12}C$:1.1% $^{13}C$ to 95% $^{12}C$:5% $^{13}C$, 90% $^{12}C$:10% $^{13}C$ or 80% $^{12}C$:20% $^{13}C$. A further example would be the isotope ratio of nitrogen, which is present in nature in a ratio of 99.6% $^{14}N$:0.4% $^{15}N$. An altered isotope ratio of nitrogen may thus include a ratio of 99.0% $^{14}N$:1.0% $^{15}N$, or 90% $^{14}N$:10% $^{15}N$, or 80% $^{14}N$:20% $^{15}N$.

The term "increased amount of an isotope" refers to the alteration of the amount of a specific isotope of a given element, which is higher than in the naturally occurring isotope distribution of said element. Exemplified, in case the isotope $^{13}C$ of the element carbon naturally occurs in 1.1% of all occurrences of the element carbon, its amount is increased if $^{13}C$ is present in e.g. 1.2%, 2%, 5% or 10% of all occurrences of the element carbon.

The term "decreased amount of an isotope" refers to the alteration of the amount of a specific isotope of a given element, which is lower than in the naturally occurring isotope distribution of said element. Exemplified, in case the isotope $^{14}C$ of the element carbon naturally occurs in 98.9% of all occurrences of the element carbon, its amount is decreased if $^{12}C$ is present in e.g. 98.8%, 98%, 95% or 90% of all occurrences of the element carbon.

In the context of the present disclosure, the term "sequencing" refers to determine the primary structure of a peptide, polypeptide or protein. Sequencing results in a symbolic linear depiction known as a sequence which succinctly summarizes much of the atomic-level structure of the sequenced molecule. Methods for performing protein sequencing include: Edman degradation, peptide mass fingerprinting, mass spectrometry, and protease digests. Typically, once the sequence of a peptide, polypeptide or protein is known, it can be readily reproduced.

In the context of the present disclosure, the term "copy protection" refers to efforts designed to prevent the reproduction of a peptide, polypeptide or protein, in particular from the identification of its sequence. The term "protection from being sequenced" refers to efforts designed to prevent the sequencing of a peptide, polypeptide or protein. Exemplified, the sequence of a protein may be identified using mass spectrometry or Edman degradation. The term copy protection thus, refers to efforts designed to prevent the identification of a protein sequence vias any of these methods, in particular via mass spectrometry.

"Mass spectrometry" ("Mass Spec" or "MS") is an analytical technique that ionizes chemical species and sorts the ions based on their mass-to-charge ratio. Following sample preparation steps, the analyte(s) of interest are separated from the matrix using e.g. gas or liquid chromatography. For the mass spectrometry measurement, the following three steps are performed:

1. a small sample is ionized, usually to cations by loss of an electron. Ionization source include but are not limited to electrospray ionization (ESI) and atmospheric pressure chemical ionization (APCI).

2. the ions are sorted and separated according to their mass and charge. High-field asymmetric-waveform ion-mobility spectrometry (FAIMS) may be used as ion filter.

3. the separated ions are then measured, and the results displayed on a chart.

Since a mass spectrometer separates and detects ions of slightly different masses, it easily distinguishes different isotopes of a given element. Mass spectrometry is thus, an important method for the accurate mass determination and characterization of analytes, including but not limited to peptides, polypeptides or proteins. Its applications include the identification of proteins and their post-translational modifications, the elucidation of protein complexes, their subunits and functional interactions, as well as the global measurement of proteins in proteomics. De novo sequencing of peptides or proteins by mass spectrometry can typically be performed without prior knowledge of the amino acid sequence.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "disease", "disorder" or "indication" are used interchangeably herein, referring to an abnormal condition, especially an abnormal medical condition such as an illness or injury, wherein a tissue, an organ or an individual is not able to efficiently fulfil its function anymore. Typically, but not necessarily, a disease is associated with specific symptoms or signs indicating the presence of such disease. The presence of such symptoms or signs may thus, be indicative for a tissue, an organ or an individual suffering from a disease. An alteration of these symptoms or signs may be indicative for the progression of such a disease. A progression of a disease is typically characterised by an increase or decrease of such symptoms or signs which may indicate a "worsening" or "bettering" of the disease. The "worsening" of a disease is characterised by a decreasing ability of a tissue, organ or organism to fulfil its function efficiently, whereas the "bettering" of a disease is typically characterised by an increase in the ability of a tissue, an organ or an individual to fulfil its function efficiently. A tissue, an organ or an individual being at "risk of developing" a disease is in a healthy state but shows potential of a disease emerging. Typically, the risk of developing a disease is associated with early or weak signs or symptoms of such disease. In such case, the onset of the disease may still be prevented by treatment. Examples of a disease include but are not limited to cardiac disease, traumatic diseases, inflammatory diseases, infectious diseases, cutaneous conditions, endocrine diseases, intestinal diseases, neurological disorders, joint diseases, genetic disorders, autoimmune diseases, and various types of cancer.

In the context of present invention, the term "biomarker" refers to a substance within a biological system that is used as an indicator of a biological state of said system. In the art, the term "biomarker" is sometimes also applied to means for the detection of said endogenous substances (e.g. antibodies, nucleic acid probes etc, imaging systems). In the context of present invention, the term "biomarker" shall be only applied for the substance, not for the detection means. Thus, biomarkers can be any kind of molecule present in a living organism, such as a nucleic acid (DNA, mRNA, miRNA, rRNA etc.), a protein (cell surface receptor, cytosolic protein etc.), a metabolite or hormone (blood sugar, insulin, estrogen, etc.), a molecule characteristic of a certain modification of another molecule (e.g. sugar moieties or phosphoryl residues on proteins, methyl-residues on genomic DNA) or a substance that has been internalized by the organism or a metabolite of such a substance.

A "kit" is any manufacture (e.g. a package or container) comprising at least one reagent, e.g., a medicament for treatment of a disorder, or a probe for specifically detecting a biomarker gene or protein of the invention. The manufacture is preferably promoted, distributed, or sold as a unit for performing the methods of the present invention. Typically, a kit may further comprise carrier means being compartmentalized to receive in close confinement one or more container means such as vials, tubes, and the like In particular, each of the container means comprises one of the separate elements to be used in the method of the first aspect. Kits may further comprise one or more other containers comprising further materials including but not limited to buffers, diluents, filters, needles, syringes, and package inserts with instructions for use. A label may be present on the container to indicate that the composition is used for a specific application, and may also indicate directions for either in vivo or in vitro use. The computer program code may be provided on a data storage medium or device such as a optical storage medium (e.g., a Compact Disc) or directly on a computer or data processing device. Moreover, the kit may, comprise standard amounts for the biomarkers as described elsewhere herein for calibration purposes.

A "package insert" is used to refer to instructions customarily included in commercial packages of therapeutic products or medicaments, that contain information about the indications, usage, dosage, administration, contraindications, other therapeutic products to be combined with the packaged product, and/or warnings concerning the use of such therapeutic products or medicaments, etc.

Embodiments

In a first aspect, the present invention relates to an antibody conjugate comprising an antibody and a tag, wherein one or more element(s) present in the antibody exhibit an isotope ratio which differs from the naturally occurring isotope ratio of said one or more element(s), wherein the amount of the isotope which is less common in nature, is increased. Accordingly, the present invention relates to an antibody conjugate comprising an antibody having an altered isotope ratio of one or more element(s) present in the antibody, and a tag. In particular said antibody has an isotope ratio of one or more element(s), wherein the amount of the isotope which is less common in nature, is increased.

In embodiments of the first aspect, the element(s) is selected from the group consisting of carbon (C), hydrogen (H), nitrogen (N), and oxygen (O). In particular embodiments, the element is carbon (C) or nitrogen (N). In particular embodiments, the element is carbon (C).

In embodiments of the first aspect, the antibody comprises an increased amount of the stable isotope $^{13}$C of the element Carbon (C). Accordingly, the antibody comprises an amount of the isotope $^{13}$C which is higher than the amount of naturally occurring $^{13}$C, i.e. which is higher than 1.1% of the overall occurrence of carbon.

In embodiments of the first aspect, the antibody comprises an increased amount of the stable isotope $^{2}$H of the element Hydrogen (H). Accordingly, the antibody comprises an amount of the isotope $^{2}$H which is higher than the amount of naturally occurring $^{2}$H, i.e. which is higher than 0.02% of the overall occurrence of Hydrogen.

In embodiments of the first aspect, the antibody comprises an increased amount of the stable isotope $^{15}$N of the element Nitrogen (N). Accordingly, the antibody comprises an amount of the isotope $^{15}$N which is higher than the amount of naturally occurring $^{15}$N, i.e. which is higher than 0.4% of the overall occurrence of Nitrogen.

In embodiments of the first aspect, the antibody comprises an increased amount of the stable isotope $^{17}$O and/or $^{18}$O of the element Oxygen (O). Accordingly, the antibody comprises an amount of the isotope $^{17}$O and/or $^{18}$O which is higher than the amount of naturally occurring $^{17}$O and/or $^{18}$O, i.e. which is higher than 0.04% or 0.2%, respectively, of the overall occurrence of Oxygen.

In embodiments of the first aspect, the amount of the isotope which is less-common in nature, is increased to at least 4% of the atoms of the respective element in the antibody.

In particular embodiments, the amount of the isotope which is less-common in nature, is increased to 6-90% of the overall occurrence of the respective atom in the antibody.

In particular embodiments, the amount of the isotope which is less-common in nature, is increased to 6-12%, in particular to 8-10%, of the overall occurrence of the respective atom in the antibody.

In particular embodiments, the amount of the isotope which is less-common in nature, is increased to 30-70%, in particular to 40-60%, of the overall occurrence of the respective atom in the antibody.

In embodiments of the first aspect, wherein the antibody comprises an increased amount of the stable isotope $^{13}$C, the amount of $^{13}$C is increased to 4-20% of the overall occurrence of carbon in the antibody. In particular embodiments, the amount of $^{13}$C is increased to 5-15% of the overall occurrence of carbon in the antibody. In particular embodiments, the amount of $^{13}$C is increased to 6-13% of the overall occurrence of carbon in the antibody. Accordingly, in particular embodiments, the amount of $^{13}$C is increased from 1.1% to at least 4%. Thus, the isotope ratio is altered from 98.9% of $^{12}$C and 1.1% of $^{13}$C to max. 96% of $^{12}$C and at least 4% of $^{13}$C. In particular embodiments, the ratio is altered from 98.9% $^{12}$C:1.1% $^{13}$C to 95% $^{12}$C:5% $^{13}$C. In particular embodiments, the ratio is altered from 98.9% $^{12}$C:1.1% $^{13}$C to 94% $^{12}$C:6% $^{13}$C. In particular embodiments, the ratio is altered from 98.9% $^{12}$C:1.1% $^{13}$C to 87% $^{12}$C:13% $^{13}$C. In particular embodiments, the ratio is altered from 98.9% $^{12}$C:1.1% $^{13}$C to 85% $^{12}$C:15% $^{13}$C. In particular embodiments, the ratio is altered from 98.9% $^{12}$C:1.1% $^{13}$C to 80% $^{12}$C:20% $^{13}$C. In particular embodiments, the ratio is altered from 98.9% $^{12}$C:1.1% $^{13}$C to 33% $^{12}$C:67% $^{13}$C. In particular embodiments, the antibody exhibits a content of 4-20%, in particular 5-15%, in particular 6% of the isotope $^{13}$C of the overall occurrence of carbon in the antibody.

In embodiments of the first aspect, wherein the antibody comprises an increased amount of the stable isotope $^{15}$N, the amount of $^{15}$N is increased to 4-96% of the overall occurrence of nitrogen in the antibody. In particular embodiments, the amount of $^{15}$N is increased to 5-95% of the overall occurrence of nitrogen in the antibody. In particular embodiments, the amount of $^{15}$N is increased to 6-94% of the overall occurrence of nitrogen in the antibody. Accordingly, in particular embodiments, the amount of $^{15}$N is increased from 0.4% to at least 4%. Thus, the isotope ratio is altered from 99.6% of $^{14}$N and 0.4% of $^{15}$N to max. 96% of $^{14}$N and at least 4% of $^{15}$N. In particular embodiments, the ratio is altered from 99.6% $^{14}$N:0.4% $^{15}$N to 95% $^{14}$N:5% $^{15}$N. In particular embodiments, the ratio is altered from 99.6% $^{14}$N:0.4% $^{15}$N to 90% $^{14}$N:10% $^{15}$N. In particular embodiments, the ratio is altered from 99.6% $^{14}$N:0.4% $^{15}$N to 80% $^{14}$N:20% $^{15}$N. In particular embodiments, the ratio is altered from 99.6% $^{14}$N:0.4% $^{15}$N to 60% $^{14}$N:40% $^{15}$N. In particular embodiments, the antibody exhibits a content of 5-95%, in particular 10-90%, I particular 20-60%, in particular 30-50% of the isotope $^{15}$N of the overall occurrence of nitrogen in the antibody.

In embodiments of the first aspect, the increased amount of the less-common stable isotope is distributed randomly in the sequence of the antibody.

In embodiments of the first aspect, the increased amount of the less-common stable isotope is incorporated in the non-essential amino acids of the antibody.

In embodiments of the first aspect, the antibody is a monoclonal antibody, polyclonal antibody, multispecific antibody (e.g., bispecific antibodies), a chimeric antibody (in particular a humanized antibody), or an antibody fragment. In embodiments of the first aspect, the antibody is a mono-specific or a multi-specific antibody. In embodiments, wherein the antibody is an antibody fragment, the antibody fragment is selected from the group consisting of a Fab, Fab', F(ab')$_2$, Fv fragments; diabodies; triabodies, sdAb, nanobodies, scFv, di-scFvs, tandem scFvs, scDb, BiTEs, DARTs.; and multispecific antibodies formed from any of these antibody fragments.

In embodiments of the first aspect, the antibody is an isolated antibody.

In embodiments of the first aspect, the antibody is a pharmaceutic antibody or a diagnostic antibody. In particular, the antibody is a diagnostic antibody specific for one or more biomarker(s) which is specific for a certain disease. In particular, the antibody is a diagnostic antibody specific for one or more biomarker(s) which is specific for a disease selected from the group consisting of cardiac disease, traumatic diseases, inflammatory diseases, infectious diseases, cutaneous conditions, endocrine diseases, intestinal diseases, neurological disorders, joint diseases, genetic disorders, autoimmune diseases, and various types of cancer In embodiments the antibody is a diagnostic antibody specific for a biomarker indicating a cardiac disease. In particular, the diagnostic antibody is directed against Troponin C or Troponin T (abbreviated: TnT or TropT).

In certain embodiments, the antibody has a dissociation constant (Kd) of $\leq 1$ µM, $\leq 100$ nM, $\leq 10$ nM, $\leq 1$ nM, $\leq 0.1$ nM, $\leq 0.01$ nM, or $\leq 0.001$ nM (e.g. 10-8 M or less, e.g. from 10-8 M to 10-13 M, e.g., from 10-9 M to 10-13 M). The Kd is measured using a BIACORE® surface plasmon resonance assay or using a radiolabeled antigen binding assay (RIA).

In embodiments of the first aspect, the tag comprised in the conjugate is a partner of a binding pair, a functional group, a therapeutic agent (drug), a cytotoxic agent (e.g. a toxin such as doxorubicin or pertussis toxin), a fluorophore (such as a fluorescent dye like fluorescein or rhodamine), a chemiluminescent tag or an electrochemiluminescent tag, a radioactive tag, a metal chelate complex for imaging or radiotherapeutic purposes, an enzyme or a fluorescent protein like GFP.

In one embodiment the tag is a partner of a binding pair. A binding pair as used herein consists of two partners binding to each other with high affinity, i.e. with one nanomolar affinity or better. Embodiments for binding pairs are for example the binding pairs consisting of receptor and ligand, hapten and anti-hapten antibody, and binding pairs based on naturally occurring high affinity binding pairs.

One example of a receptor-ligand binding pair is a pair consisting of a steroid hormone receptor and the corresponding steroid hormone.

One type of a binding pair which is suitable for the present invention is a hapten and anti-hapten antibody binding pair. A hapten is an organic molecule with a molecular weight of 100 to 2000 Dalton, preferably of 150 to 1000 Dalton. Such small molecule can be rendered immunogenic by coupling it to a carrier molecule and anti-hapten antibodies can be generated according to standard procedures. The hapten may be selected from the group comprising sterols, bile acids, sexual hormones, corticoids, cardenolides, cardenolide-glycosides, bufadienolides, steroid-sapogenines and steroid alkaloids, cardenolides and cardenolide-glycosides. Representatives of these substance classes are digoxigenin, digitoxigenin, gitoxigenin, strophanthidin, digoxin, digitoxin, ditoxin, strophanthin. Another suitable hapten is for example fluorescein.

Examples of binding pairs based on naturally occurring high affinity binding pairs are biotin or biotin analogues such as aminobiotin, iminobiotin or desthiobiotin and avidin or streptavidin as well as the FimG and DsF binding pair. The biotin-(strept)avidin binding pair is well-known in the art. The basic principles of the FimG-DsF binding pair are e.g. described in WO2012/028697.

In one embodiment binding pairs are selected from hapten and anti-hapten antibody, biotin or biotin analogues such as aminobiotin, iminobiotin or desthiobiotin and avidin or streptavidin, FimG and DsF, and receptor and ligand.

In one embodiment binding pairs are selected from hapten and anti-hapten antibody and biotin or biotin analogues such as aminobiotin, iminobiotin or desthiobiotin/avidin or streptavidin, FimG and DsF.

In one embodiment the binding pair is biotin (or biotin analogues such as aminobiotin, iminobiotin or desthiobiotin) and avidin or streptavidin.

In one embodiment the binding pair consists of biotin and streptavidin.

In one embodiment the tag is a functional group selected from the group consisting of aldehyde, carboxylic acid, carboxylic acid ester, epoxide, N-hydroxysuccinimide ester, amino group, halogen, hydrazine, hydroxyl, sulfhydryl, maleimido, alkynyl, azide, isocyanate, isothiocyanate and phosphoramidite, trans-cyclooctene, tetrazine.

In one embodiment, the tag is a functional group selected from the group consisting of carboxylic acid, N-hydroxysuccinimide ester, amino group, halogen, sulfhydryl, maleimido, alkynyl, azide, isocyanate, isothiocyanate and phosphoramidite.

In one embodiment, the tag is a therapeutic agent (drug) and may e.g. be an antibody or an antigen-binding fragment thereof. A number of therapeutic antibodies directed against cell surface molecules and their ligands are known, such as Rituxan/MabThera/Rituximab, 2H7/Ocrelizumab, Zevalin/Ibrizumomab, Arzerra/Ofatumumab (CD20), HLL2/Epratuzumab, Inotuzomab (CD22), Zenapax/Daclizumab, Simulect/Basiliximab (CD25), Herceptin/Trastuzumab, Pertuzumab (Her2/ERBB2), Mylotarg/Gemtuzumab (CD33), Raptiva/Efalizumab (Cd11a), Erbitux/Cetuximab (EGFR, epidermal growth factor receptor), IMC-1121B (VEGF receptor 2), Tysabri/Natalizumab ($\alpha$4-subunit of $\alpha$4$\beta$1 and $\alpha$4$\beta$7 integrins), ReoPro/Abciximab (gpIIb-gpIIa and $\alpha$v$\beta$3-integrin), Orthoclone OKT3/Muromonab-CD3 (CD3), Benlysta/Belimumab (BAFF), Tolerx/Oteliximab (CD3), Soliris/Eculizumab (C5 complement protein), Actemra/Tocilizumab (IL-6R), Panorex/Edrecolomab (EpCAM, epithelial cell adhesion molecule), CEA-CAM5/Labetuzumab (CD66/CEA, carcinoembryonic antigen), CT-11 (PD-1, programmed death-1 T-cell inhibitory receptor, CD-d279), H224G11 (c-Met receptor), SAR3419 (CD19), IMC-A12/Cixutumumab (IGF-1R, insulin-like growth factor 1 receptor), MEDI-575 (PDGF-R, platelet-derived growth factor receptor), CP-675, 206/Tremelimumab (cytotoxic T lymphocyte antigen 4), RO5323441 (placenta growth factor or PGF), HGS1012/Mapatumumab (TRAIL-R1), SGN-70 (CD70), Vedotin(SGN-35)/Brentuximab (CD30), and ARH460-16-2 (CD44).

In a further embodiment, the tag is a cytotoxic agent selected from: (i) chemotherapeutic agents, which may function as microtubule inhibitors, mitosis inhibitors, topoisomerase inhibitors, or DNA intercalators; (ii) protein toxins, which may function enzymatically; and (iii) therapeutic radioisotopes.

Chemotherapeutic agents include, but are not limited to, a maytansinoid, an auristatin, a dolastatin, a trichothecene, CC1065, a calicheamicin and other enediyne antibiotics, a taxane, an anthracycline, and stereoisomers, isosters, analogs or derivatives thereof.

Protein toxins include but are not limited to, diphtheria-A chain, non-binding active fragments of diphtheria toxin, exotoxin A chain (from *Pseudomonas aeruginosa*), ricin A chain (Vitetta et al (1987) Science, 238:1098), abrin A chain, modeccin A chain, alpha-sarcin, *Aleurites fordii* proteins, dianthin proteins, *Phytolaca americana* proteins (PAPI, PAPII, and PAP-5), *Momordica charantia* inhibitor, curcin, crotin, sapaonaria *officinalis* inhibitor, gelonin, mitogellin, restrictocin, phenomycin, enomycin, and the tricothecenes (WO 93/21232).

Therapeutic radioisotopes include 32P, 33P, 90Y, 125I, 131I, 131In, 153Sm, 186Re, 188Re, 211At, 212B, 212Pb, and radioactive isotopes of Lu. The radioisotope may be incorporated in known ways (Fraker et al (1978) Biochem. Biophys. Res. Commun. 80: 49-57; "Monoclonal Antibodies in Immunoscintigraphy" Chatal, CRC Press 1989). Carbon-14-labeled 1-isothiocyanatobenzyl-3-methyldiethylene triamine pentaacetic acid (MX-DTPA) is an exemplary chelating agent for conjugation of a radionuclide to the complex (WO 94/11026).

In one embodiment the tag may function to: (i) provide a detectable signal; (ii) interact with a second label to modify the detectable signal provided by the first or second label, e.g. to give FRET (fluorescence resonance energy transfer); (iii) affect mobility, e.g. electrophoretic mobility or cell-permeability, by charge, hydrophobicity, shape, or other physical parameters, or (iv) provide a capture moiety, e.g. to modulate ionic complexation.

Numerous tags which provide a detectable signal are available and can be generally grouped into the following categories:

(a) Fluorescent tags or fluorophores,
(b) chemiluminescent dyes (Briggs et al "Synthesis of Functionalized Fluorescent Dyes and Their Coupling to Amines and Amino Acids," J. Chem. Soc., Perkin-Trans. 1 (1997) 1051-1058), and
(c) electrochemiluminescent tags.

Fluorescent tags or fluorophores include rare earth chelates (europium chelates), fluorescein type tag (including FITC, 5-carboxyfluorescein, 6-carboxy fluorescein); rhodamine type tags including TAMRA; dansyl; Lissamine; cyanines; phycoerythrins; Texas Red; and analogs thereof. The fluorescent tag may be conjugated to using the techniques disclosed in Current Protocols in Immunology, supra, for example. Fluorescent dyes and fluorescent tag reagents include those which are commercially available e.g. from Invitrogen/Molecular Probes (Eugene, Oreg., USA) and Pierce Biotechnology, Inc. (Rockford, Ill.).

The different classes of chemiluminogenic tags include luminol, acridinium compounds, coelenterazine and analogues, dioxetanes, systems based on peroxyoxalic acid and their derivatives. For immunodiagnostic procedures predominantly acridinium based tags are used (a detailed overview is given in Dodeigne C. et al., Talanta 51 (2000) 415-439).

The tags of major relevance as electrochemiluminescent tags are the Ruthenium- and the Iridium-based electrochemiluminescent complexes, respectively. Electrochemiluminescense (ECL) proved to be very useful in analytical applications as a highly sensitive and selective method. It combines analytical advantages of chemiluminescent analysis (absence of background optical signal) with ease of reaction control by applying electrode potential. In general Ruthenium complexes, especially [Ru (Bpy)3]2+ (which releases a photon at ~620 nm) regenerating with TPA (Tripropylamine) in liquid phase or liquid-solid interface are used as ECL-labels. Recently also Iridium-based ECL-labels have been described (WO2012107419(A1)).

Metal-chelate complexes suitable as labels for imaging and therapeutic purposes are well-known in the art (US 2010/0111856; U.S. Pat. Nos. 5,342,606; 5,428,155; 5,316, 757; 5,480,990; 5,462,725; 5,428,139; 5,385,893; 5,739, 294; 5,750,660; 5,834,456; Hnatowich et al, J. Immunol. Methods 65 (1983) 147-157; Meares et al, Anal. Biochem. 142 (1984) 68-78; Mirzadeh et al, Bioconjugate Chem. 1 (1990) 59-65; Meares et al, J. Cancer (1990), Suppl. 10:21- 26; Izard et al, Bioconjugate Chem. 3 (1992) 346-350; Nikula et al, Nucl. Med. Biol. 22 (1995) 387-90; Camera et al, Nucl. Med. Biol. 20 (1993) 955-62; Kukis et al, J. Nucl. Med. 39 (1998) 2105-2110; Verel et al., J. Nucl. Med. 44 (2003) 1663-1670; Camera et al, J. Nucl. Med. 21 (1994) 640-646; Ruegg et al, Cancer Res. 50 (1990) 4221-4226; Verel et al, J. Nucl. Med. 44 (2003) 1663-1670; Lee et al, Cancer Res. 61 (2001) 4474-4482; Mitchell, et al, J. Nucl. Med. 44 (2003) 1105-1112; Kobayashi et al Bioconjugate Chem. 10 (1999) 103-111; Miederer et al, J. Nucl. Med. 45 (2004) 129-137; DeNardo et al, Clinical Cancer Research 4 (1998) 2483-90; Blend et al, Cancer Biotherapy & Radiopharmaceuticals 18 (2003) 355-363; Nikula et al J. Nucl. Med. 40 (1999) 166-76; Kobayashi et al, J. Nucl. Med. 39 (1998) 829-36; Mardirossian et al, Nucl. Med. Biol. 20 (1993) 65-74; Roselli et al, Cancer Biotherapy & Radiopharmaceuticals, 14 (1999) 209-20).

Enzymes also may be used as a tag. Various enzyme-substrate label systems are available. The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazindiones, malate dehydrogenase, urease, peroxidase such as horseradish peroxidase (HRP), alkaline phosphatase (AP), (3-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

Examples of enzyme-substrate combinations (see also U.S. Pat. Nos. 4,275,149; 4,318,980) include, for example:

(i) Horseradish peroxidase (HRP) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB));

(ii) alkaline phosphatase (AP) with para-nitrophenyl phosphate as chromogenic substrate; and (iii) (3-D-galactosidase ((3-D-Gal) with a chromogenic substrate (e.g., p-nitro phenyl-(3-D-galactosidase) or fluorogenic substrate 4-methylumbelliferyl-(3-D-galactosidase.

In a second aspect, the present invention relates to the use of a conjugate as described in detail above for the first aspect of the invention, for preventing the sequencing of the comprised antibody.

In particular embodiments, the conjugate is used to prevent the sequencing of the comprised antibody via mass spectrometry.

In a third aspect, the present invention relates to the use of a stable isotopic label for protecting the sequence of an antibody, from being determined, in particular from being sequenced. In particular embodiments, the stable isotopic label is used to prevent the sequencing of an antibody, via mass spectrometry. In particular embodiments of the third aspect, the stable isotopic label is created by altering, in particular by increasing, the amount of a stable isotope of a specific element in an antibody, in particular in an antibody comprised in an antibody conjugate.

In embodiments of the third aspect, the element(s) whose stable isotope is altered, in particular increased, is selected from the group consisting of carbon (C), hydrogen (H), nitrogen (N), and oxygen (O). In particular embodiments, the element is carbon (C) or nitrogen (N). In particular embodiments, the element is carbon (C).

In embodiments of the third aspect, an increased amount of the stable isotope $^{13}$C of the element Carbon (C) is used to for protecting the sequence of an antibody, from being determined. Accordingly, an amount of the stable isotope $^{13}$C which is higher than the amount of naturally occurring $^{13}$C, i.e. which is higher than 1.1% of the overall occurrence of carbon, is used for protecting the sequence of an antibody, from being determined. In embodiments of the third aspect, an increased amount of the stable isotope $^2$H of the element Hydrogen (H) is used to for protecting the sequence of an antibody, from being determined. Accordingly, an amount of the stable isotope $^2$H which is higher than the amount of naturally occurring $^2$H, i.e. which is higher than 0.02% of the overall occurrence of Hydrogen is used for protecting the sequence of an antibody, from being determined.

In embodiments of the third aspect, an increased amount of the stable isotope $^{15}$N of the element Nitrogen (N) is used to for protecting the sequence of an antibody, from being determined. Accordingly, an amount of the stable isotope $^{15}$N which is higher than the amount of naturally occurring $^{15}$N, i.e. which is higher than 0.4% of the overall occurrence of Nitrogen is used for protecting the sequence of an antibody, from being determined.

In embodiments of the third aspect, an increased amount of the stable isotope $^{17}$O, and/or $^{18}$O of the element Oxygen (O) is used to for protecting the sequence of an antibody, from being determined. Accordingly, an amount of the stable isotope $^{17}$O and/or $^{18}$O which is higher than the amount of naturally occurring $^{17}$O and/or $^{18}$O, i.e. which is higher than 0.04% or 0.2%, respectively, of the overall occurrence of Oxygen is used for protecting the sequence of an antibody, from being determined.

In embodiments of the third aspect, the amount of the isotope which is less-common in nature, is increased to at least 4% of the atoms of the respective element in the antibody.

In particular embodiments, the amount of the isotope which is less-common in nature, is increased to 6-90% of the overall occurrence of the respective element in the antibody.

In particular embodiments, the amount of the isotope which is less-common in nature, is increased to 6-12%, in particular to 8-10%, of the overall occurrence of the respective element in the antibody.

In particular embodiments, the amount of the isotope which is less-common in nature, is increased to 30-70%, in particular to 40-60%, of the overall occurrence of the respective element in the antibody.

In embodiments of the third aspect, wherein an increased amount of the stable isotope $^{13}$C is used, the amount of $^{13}$C is increased to 4-20% of the overall occurrence of carbon in the antibody. In particular embodiments, the amount of $^{13}$C is increased to 5-15% of the overall occurrence of carbon in the antibody. In particular embodiments, the amount of $^{13}$C is increased to 6-13% of the overall occurrence of carbon in the antibody. Accordingly, in particular embodiments, the amount of $^{13}$C is increased from 1.1% to at least 4%. Thus, the isotope ratio is altered from 98.9% of $^{12}$C and 1.1% of $^{13}$C to max. 96% of $^{12}$C and at least 4% of $^{13}$C. In particular embodiments, the ratio is altered from 98.9% $^{12}$C:1.1% $^{13}$C to 95% $^{12}$C:5% $^{13}$C. In particular embodiments, the ratio is altered from 98.9% $^{12}$C:1.1% $^{13}$C to 94% $^{12}$C:6% $^{13}$C. In particular embodiments, the ratio is altered from 98.9% $^{12}$C:1.1% $^{13}$C to 87% $^{12}$C:13% $^{13}$C. In particular embodiments, the ratio is altered from 98.9% $^{12}$C:1.1% $^{13}$C to 85% $^{12}$C:15% $^{13}$C. In particular embodiments, the ratio is altered from 98.9% $^{12}$C:1.1% $^{13}$C to 80% $^{12}$C:20% $^{13}$C. In particular embodiments, the ratio is altered from 98.9% $^{12}$C:1.1% $^{13}$C to 33% $^{12}$C:67% $^{13}$C. In particular embodiments, the antibody exhibits a content of 4-20%, in particular 5-15%, in particular 6% of the isotope $^{13}$C of the overall occurrence of carbon in the antibody.

In embodiments of the third aspect, wherein an increased amount of the stable isotope $^{15}$N is used, the amount of $^{15}$N is increased to 4-96% of the overall occurrence of nitrogen in the antibody. In particular embodiments, the amount of $^{15}$N is increased to 5-95% of the overall occurrence of nitrogen in the antibody. In particular embodiments, the amount of $^{15}$N is increased to 6-94% of the overall occurrence of nitrogen in the antibody. Accordingly, in particular embodiments, the amount of $^{15}$N is increased from 0.4% to at least 4%. Thus, the isotope ratio is altered from 99.6% of $^{14}$N and 0.4% of $^{15}$N to max. 96% of $^{14}$N and at least 4% of $^{15}$N. In particular embodiments, the ratio is altered from 99.6% $^{14}$N:0.4% $^{15}$N to 95% $^{14}$N:5% $^{15}$N. In particular embodiments, the ratio is altered from 99.6% $^{14}$N:0.4% $^{15}$N to 90% $^{14}$N:10% $^{15}$N. In particular embodiments, the ratio is altered from 99.6% $^{14}$N:0.4% $^{15}$N to 80% $^{14}$N:20% $^{15}$N. In particular embodiments, the ratio is altered from 99.6% $^{14}$N:0.4% $^{15}$N to 60% $^{14}$N:40% $^{15}$N. In particular embodiments, the antibody exhibits a content of 5-95%, in particular 10-90%, I particular 20-60%, in particular 30-50% of the isotope $^{15}$N of the overall occurrence of nitrogen in the antibody.

In embodiments of the third aspect, the increased amount of the less-common stable isotope is distributed randomly in the sequence of the antibody.

In embodiments of the third aspect, the increased amount of the less-common stable isotope is incorporated in the non-essential amino acids of the antibody.

In embodiments of the third aspect, the antibody is a monoclonal antibody, polyclonal antibody, multispecific antibody (e.g., bispecific antibodies), a chimeric antibody (in particular a humanized antibody), or an antibody fragment. In embodiments of the third aspect, the antibody is a monospecific or a multi-specific antibody. In embodiments, wherein the antibody is an antibody fragment, the antibody fragment is selected from the list consisting of a Fab, Fab', F(ab')$_2$, Fv fragments; diabodies; triabodies, sdAb, nanobodies, scFv, di-scFvs, tandem scFvs, scDb, BiTEs, DARTs.; and multispecific antibodies formed from any of these antibody fragments.

In embodiments of the third aspect, the antibody is an isolated antibody.

In embodiments of the third aspect, the antibody is a pharmaceutic antibody or a diagnostic antibody. In particular, the antibody is a diagnostic antibody specific for one or more biomarker(s) which is specific for a certain disease. In particular, the antibody is a diagnostic antibody specific for one or more biomarker(s) which is specific for a disease selected from the group consisting of cardiac disease, traumatic diseases, inflammatory diseases, infectious diseases, cutaneous conditions, endocrine diseases, intestinal diseases, neurological disorders, joint diseases, genetic disorders, autoimmune diseases, and various types of cancer In embodiments, the antibody is a diagnostic antibody specific for a biomarker indicating a cardiac disease. In particular, the diagnostic antibody is directed against Troponin C or T.

In certain embodiments, the antibody has a dissociation constant (Kd) of ≤1 μM, ≤100 nM, ≤10 nM, ≤1 nM, ≤0.1 nM, ≤0.01 nM, or ≤0.001 nM (e.g. 10-8 M or less, e.g. from 10-8 M to 10-13 M, e.g., from 10-9 M to 10-13 M). The Kd is measured using a BIACORE® surface plasmon resonance assay or using a radiolabeled antigen binding assay (RIA).

In embodiments of the third aspect, the tag comprised in the complex is a partner of a binding pair, a functional group, a therapeutic agent (drug), a cytotoxic agent (e.g. a toxin such as doxorubicin or pertussis toxin), a fluorophore (such as a fluorescent dye like fluorescein or rhodamine), a chemiluminescent tag or an electrochemiluminescent tag, a radioactive tag, a metal chelate complex for imaging or radiotherapeutic purposes, an enzyme or a fluorescent protein like GFP.

In one embodiment the tag is a partner of a binding pair. A binding pair as used herein consists of two partners binding each other with high affinity, i.e. with one nanomolar affinity or better. Embodiments for binding pairs are for example the binding pairs consisting of receptor and ligand, hapten and anti-hapten antibody, and binding pairs based on naturally occurring high affinity binding pairs.

One example of a receptor-ligand binding pair is a pair consisting of a steroid hormone receptor and the corresponding steroid hormone.

One type of a binding pair which is suitable for the present invention is a hapten and anti-hapten antibody binding pair. A hapten is an organic molecule with a molecular weight of 100 to 2000 Dalton, preferably of 150 to 1000 Dalton. Such small molecule can be rendered immunogenic by coupling it to a carrier molecule and anti-hapten antibodies can be generated according to standard procedures. The hapten may be selected from the group comprising sterols, bile acids, sexual hormones, corticoids, cardenolides, cardenolide-glycosides, bufadienolides, steroid-sapogenines and steroid alkaloids, cardenolides and cardenolide-glycosides. Representatives of these substance classes are digoxigenin, digitoxigenin, gitoxigenin, strophanthidin, digoxin, digitoxin, ditoxin, strophanthin. Another suitable hapten is for example fluorescein.

Examples of binding pairs based on naturally occurring high affinity binding pairs are biotin or biotin analogues such as aminobiotin, iminobiotin or desthiobiotin and avidin or streptavidin as well as the FimG and DsF binding pair. The biotin-(strept)avidin binding pair is well-known in the art. The basic principles of the FimG-DsF binding pair are e.g. described in WO2012/028697.

In one embodiment binding pairs are selected from hapten and anti-hapten antibody, biotin or biotin analogues such as aminobiotin, iminobiotin or desthiobiotin and avidin or streptavidin, FimG and DsF, and receptor and ligand.

In one embodiment binding pairs are selected from hapten and anti-hapten antibody and biotin or biotin analogues such as aminobiotin, iminobiotin or desthiobiotin/avidin or streptavidin, FimG and DsF.

In one embodiment the binding pair is biotin (or biotin analogues such as aminobiotin, iminobiotin or desthiobiotin) and avidin or streptavidin.

In one embodiment the binding pair consists of biotin and streptavidin.

In one embodiment the tag is a functional group selected from the group consisting of aldehyde, carboxylic acid, carboxylic acid ester, epoxide, N-hydroxysuccinimide ester, amino group, halogen, hydrazine, hydroxyl, sulfhydryl, maleimido, alkynyl, azide, isocyanate, isothiocyanate and phosphoramidite, trans-cyclooctene, tetrazine.

In one embodiment, the tag is a functional group selected from the group consisting of carboxylic acid, N-hydroxysuccinimide ester, amino group, halogen, sulfhydryl, maleimido, alkynyl, azide, isocyanate, isothiocyanate and phosphoramidite.

In one embodiment, the tag is a therapeutic agent (drug) and may e.g. be an antibody or an antigen-binding fragment thereof. A number of therapeutic antibodies directed against cell surface molecules and their ligands are known, such as Rituxan/MabThera/Rituximab, 2H7/Ocrelizumab, Zevalin/Ibrizumomab, Arzerra/Ofatumumab (CD20), HLL2/Epratuzumab, Inotuzomab (CD22), Zenapax/Daclizumab, Simulect/Basiliximab (CD25), Herceptin/Trastuzumab, Pertuzumab (Her2/ERBB2), Mylotarg/Gemtuzumab (CD33), Raptiva/Efalizumab (Cd11a), Erbitux/Cetuximab (EGFR, epidermal growth factor receptor 2), IMC-1121B (VEGF receptor 2), Tysabri/Natalizumab (α4-subunit of α4β1 and α4β7 integrins), ReoPro/Abciximab (gpIIb-gpIIa and αvβ3-integrin), Orthoclone OKT3/Muromonab-CD3 (CD3), Benlysta/Belimumab (BAFF), Tolerx/Oteliximab (CD3), Soliris/Eculizumab (C5 complement protein), Actemra/Tocilizumab (IL-6R), Panorex/Edrecolomab (EpCAM, epithelial cell adhesion molecule), CEA-CAM5/Labetuzumab (CD66/CEA, carcinoembryonic antigen), CT-11 (PD-1, programmed death-1 T-cell inhibitory receptor, CD-d279), H224G11 (c-Met receptor), SAR3419 (CD19), IMC-A12/Cixutumumab (IGF-1R, insulin-like growth factor 1 receptor), MEDI-575 (PDGF-R, platelet-derived growth factor receptor), CP-675, 206/Tremelimumab (cytotoxic T lymphocyte antigen 4), RO5323441 (placenta growth factor or PGF), HGS1012/Mapatumumab (TRAIL-R1), SGN-70 (CD70), Vedotin (SGN-35)/Brentuximab (CD30), and ARH460-16-2 (CD44).

In a further embodiment, the tag is a cytotoxic agent selected from: (i) chemotherapeutic agents, which may function as microtubule inhibitors, mitosis inhibitors, topoisomerase inhibitors, or DNA intercalators; (ii) protein toxins, which may function enzymatically; and (iii) therapeutic radioisotopes.

Chemotherapeutic agents include, but are not limited to, a maytansinoid, an auristatin, a dolastatin, a trichothecene, CC1065, a calicheamicin and other enediyne antibiotics, a taxane, an anthracycline, and stereoisomers, isosters, analogs or derivatives thereof.

Protein toxins include but are not limited to, diphtheria-A chain, non-binding active fragments of diphtheria toxin, exotoxin A chain (from *Pseudomonas aeruginosa*), ricin A chain (Vitetta et al (1987) Science, 238:1098), abrin A chain, modeccin A chain, alpha-sarcin, *Aleurites fordii* proteins, dianthin proteins, *Phytolaca americana* proteins (PAPI, PAPII, and PAP-5), *Momordica charantia* inhibitor, curcin, crotin, sapaonaria *officinalis* inhibitor, gelonin, mitogellin, restrictocin, phenomycin, enomycin, and the tricothecenes (WO 93/21232).

Therapeutic radioisotopes include 32P, 33P, 90Y, 125I, 131I, 131In, 153Sm, 186Re, 188Re, 211At, 212B, 212Pb, and radioactive isotopes of Lu. The radioisotope may be incorporated in known ways (Fraker et al (1978) Biochem. Biophys. Res. Commun. 80: 49-57; "Monoclonal Antibodies in Immunoscintigraphy" Chatal, CRC Press 1989). Carbon-14-labeled 1-isothiocyanatobenzyl-3-methyldiethylene triamine pentaacetic acid (MX-DTPA) is an exemplary chelating agent for conjugation of a radionuclide to the complex (WO 94/11026).

In one embodiment the tag may function to: (i) provide a detectable signal; (ii) interact with a second label to modify the detectable signal provided by the first or second label, e.g. to give FRET (fluorescence resonance energy transfer); (iii) affect mobility, e.g. electrophoretic mobility or cell-permeability, by charge, hydrophobicity, shape, or other physical parameters, or (iv) provide a capture moiety, e.g. to modulate ionic complexation.

Numerous tags which provide a detectable signal are available and can be generally grouped into the following categories:

(a) Fluorescent tags or fluorophores,
(b) chemiluminescent dyes (Briggs et al "Synthesis of Functionalized Fluorescent Dyes and Their Coupling to Amines and Amino Acids," J. Chem. Soc., Perkin-Trans. 1 (1997) 1051-1058), and
(c) electrochemiluminescent tags.

Fluorescent tags or fluorophores include rare earth chelates (europium chelates), fluorescein type tag (including FITC, 5-carboxyfluorescein, 6-carboxy fluorescein); rhodamine type tags including TAMRA; dansyl; Lissamine; cyanines; phycoerythrins; Texas Red; and analogs thereof. The fluorescent tag may be conjugated to using the techniques disclosed in Current Protocols in Immunology, supra, for example. Fluorescent dyes and fluorescent tag reagents include those which are commercially available e.g. from Invitrogen/Molecular Probes (Eugene, Oreg., USA) and Pierce Biotechnology, Inc. (Rockford, Ill.).

The different classes of chemiluminogenic tags include luminol, acridinium compounds, coelenterazine and analogues, dioxetanes, systems based on peroxyoxalic acid and their derivatives. For immunodiagnostic procedures predominantly acridinium based tags are used (a detailed overview is given in Dodeigne C. et al., Talanta 51 (2000) 415-439).

The tags of major relevance as electrochemiluminescent tags are the Ruthenium- and the Iridium-based electrochemiluminescent complexes, respectively. Electrochemiluminescense (ECL) proved to be very useful in analytical applications as a highly sensitive and selective method. It combines analytical advantages of chemiluminescent analysis (absence of background optical signal) with ease of reaction control by applying electrode potential. In general Ruthenium complexes, especially [Ru (Bpy)3]2+ (which releases a photon at ~620 nm) regenerating with TPA (Tripropylamine) in liquid phase or liquid-solid interface are used as ECL-labels. Recently also Iridium-based ECL-labels have been described (WO2012107419(A1)).

Metal-chelate complexes suitable as labels for imaging and therapeutic purposes are well-known in the art (US 2010/0111856; U.S. Pat. Nos. 5,342,606; 5,428,155; 5,316,757; 5,480,990; 5,462,725; 5,428,139; 5,385,893; 5,739,294; 5,750,660; 5,834,456; Hnatowich et al, J. Immunol. Methods 65 (1983) 147-157; Meares et al, Anal. Biochem. 142 (1984) 68-78; Mirzadeh et al, Bioconjugate Chem. 1 (1990) 59-65; Meares et al, J. Cancer (1990), Suppl. 10:21-26; Izard et al, Bioconjugate Chem. 3 (1992) 346-350; Nikula et al, Nucl. Med. Biol. 22 (1995) 387-90; Camera et al, Nucl. Med. Biol. 20 (1993) 955-62; Kukis et al, J. Nucl. Med. 39 (1998) 2105-2110; Verel et al., J. Nucl. Med. 44 (2003) 1663-1670; Camera et al, J. Nucl. Med. 21 (1994) 640-646; Ruegg et al, Cancer Res. 50 (1990) 4221-4226; Verel et al, J. Nucl. Med. 44 (2003) 1663-1670; Lee et al, Cancer Res. 61 (2001) 4474-4482; Mitchell, et al, J. Nucl. Med. 44 (2003) 1105-1112; Kobayashi et al Bioconjugate Chem. 10 (1999) 103-111; Miederer et al, J. Nucl. Med. 45 (2004) 129-137; DeNardo et al, Clinical Cancer Research 4 (1998) 2483-90; Blend et al, Cancer Biotherapy & Radiopharmaceuticals 18 (2003) 355-363; Nikula et al J. Nucl. Med. 40 (1999) 166-76; Kobayashi et al, J. Nucl. Med. 39 (1998) 829-36; Mardirossian et al, Nucl. Med. Biol. 20 (1993) 65-74; Roselli et al, Cancer Biotherapy & Radiopharmaceuticals, 14 (1999) 209-20).

Enzymes also may be used as a tag. Various enzyme-substrate label systems are available. The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazindiones, malate dehydrogenase, urease, peroxidase such as horseradish peroxidase (HRP), alkaline phosphatase (AP), (3-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of enzyme-substrate combinations (see also U.S. Pat. Nos. 4,275,149; 4,318,980) include, for example:

(i) Horseradish peroxidase (HRP) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB));

(ii) alkaline phosphatase (AP) with para-nitrophenyl phosphate as chromogenic substrate; and (iii) (3-D-galactosidase ((3-D-Gal) with a chromogenic substrate (e.g., p-nitro phenyl-(3-D-galactosidase) or fluorogenic substrate 4-methylumbelliferyl-(3-D-galactosidase.

In a fourth aspect, the present invention relates to a kit comprising at least one conjugate as specified above with respect to the first aspect of the invention, for determining the presence and/or amount of a biomarker. In particular embodiments, the kit comprises two conjugates as specified above with respect to the first aspect of the invention.

In particular embodiments, said kit comprises a first and a second conjugate as specified in the first aspect of the present invention. In embodiments, the first and the second conjugate are capable of binding to the same antigens. In particular, the binding of said first and of said second conjugate does not interfere with each other. In embodiments, one of said conjugates is bound to or capable of binding to a solid phase and the other of said antibodies or antigen-binding fragment thereof, is detectably labeled. Accordingly, in a fourth aspect, the present invention relates to a kit for measuring the level of an biomarker, the kit comprising: a first and a second conjugate wherein said first and said second conjugate are capable of binding to said antigen, and wherein the binding of said first and of said second conjugate does not interfere with each other, wherein one of said conjugates is bound to or capable of binding to a solid phase and wherein the other of said conjugates is detectably tagged.

In embodiments, the kit further comprises carrier means being compartmentalized to receive in close confinement one or more container means selected from the group consisting of vials and tubes. In particular embodiment, the container means further comprise one of several separate elements to be used, in particular those selected from the group consisting of buffers, diluents, filters, needles, syringes, and package inserts with instructions for use. A label may be present on the container to indicate that the composition is used for a specific application, and may also indicate directions for either in vivo or in vitro use.

In particular embodiments, the kit comprises at least one container, a label on said at least one container, and a composition contained within said at least one container, wherein the composition includes at least one conjugate that binds to a biomarker. In particular, the label on said container indicates that the composition can be used to evaluate the presence of the biomarker in a sample. In particular, the kit includes instructions for using the conjugate for evaluating the presence of a biomarker in a particular sample type. The kit may further comprise a set of instructions and materials for preparing a sample and applying the conjugate to the sample.

In particular embodiments, the kit comprises one container comprising the first conjugate and the second conjugate as specified above within the context of the first aspect.

In particular embodiments, the kit comprises two containers, wherein the first container comprises the first conjugate, and wherein the second container comprises the second conjugate, as specified above within the context of the first aspect.

In further embodiments, the kits also comprises components selected from the group consisting of one or more buffers (e.g., block buffer, wash buffer, substrate buffer, etc.), other reagents such as substrate (e.g., chromogen) that is chemically altered by an enzymatic label, epitope retrieval solution, control samples (positive and/or negative controls), control slide(s), etc. Kits can also include instructions for interpreting the results obtained using the kit.

EXAMPLES

Example 1

Antibody Labeling and Mass Spec Analysis

The antibody "MAK 11-7, anti-Troponin T" was expressed by utilization of a mouse-hybridoma clone (single cell of a mouse spleen fused to a myeloma cell (P3×63-Ag8.653)) in the presence of normal or C13-Glucose enriched RPMI medium (Gibco Cat. No. 31870-025), +2 g/L Glucose (normal or 13C) and 5% fetal calf serum. The corresponding hybridoma cells were incubated for 7 days at 37° C. and 6% $CO_2$.

After harvesting the cells, culture supernatant containing the desired antibody was isolated and transferred for tandem MS/MS analysis. In detail, the antibody in FCS-matrix (fetal calf serum) was reduced for 30 min at 50° C. with DTT, free SH groups carbamidomethylated at room temperature in the dark and digested for 18 hours at 37° C. using Trypsin. The peptides were separated chromatographically via acetonitrile gradient elution IP-RP-HPLC having a total run time of 45 min and analyzed in data-dependent tandem MS/MS mode using an FTICR from Thermofisher (FIG. 1). Experimental data was evaluated using Mascot (database search algorithm) which compares experimental data with theoretically calculated data. Data was searched against an inhouse generated database including target sequence and known "contaminants" using standard parameters (Enzyme: Trypsin; maximum number of missed cleavages=2; Precursor mass tolerance: 10 ppm; fragment tolerance: 0.8 m/z; static modification: carbamidomethylation; variable modification: oxidation). The obtained results are represented as a probability-based list of peptide sequences. As shown in FIG. 1A 38% each of the light chain and heavy chain could be clearly identified. In contrast, only 2% of the heavy chain and 0% of the light chain of the C13-labeled antibody could be clearly identified (see FIG. 1B).

Trypsin digestion of the heavy chain generates for example peptide fragment NTQPIMDTDGSYFVYSK. Theoretical calculation of the isotope distribution for different ratios of $^{12}C$ to $^{13}C$ of the double positively charged $[M+2H]^{2+}$ peptide result in the spectra as shown in FIG. 2 (calculation performed using IsoPro in Version 3.0).

Comparison to the measured data reveals expression medium dependent isotope distributions of the peptide as shown in FIG. 3A. In the heavy medium it corresponds to an incorporation of approximately 6% $^{13}C$ (see FIG. 3B). Thus, already an incorporation of 6% or $^{13}C$ (in comparison to the normally occurring 1.1%) prevents the identification of the peptide. This suggests that also the de novo sequencing, which requires a much higher experimental data quality would not be successful. In such case, already the incorporation of less than 6% $^{13}C$ would protect the antibody.

Example 2

Biomolecular Interaction Analysis

To analyse the functionality, i.e. the binding activity, of the C13-labeled anti-troponin T antibody to its antigen, the Kd was measured using a BIACORE® surface plasmon resonance assay at 37° C. Results are given in FIG. 5 showing that the C13 labeled antibody exhibits the same Kd value as the normal, non-labeled antibody, i.e. exhibits the same binding affinity.

Detailed kinetic investigations were performed at 37° C. on a GE Healthcare T200 instrument. A Biacore CM5 series S sensor was mounted into the instrument and was hydrodynamically addressed and preconditioned according to the manufacturer's instructions. The system buffer was PBS-DT (PBS pH 7.4, 0.05% DMSO, 0.05% Tween20 (w/v)). The sample buffer was the system buffer supplemented with 1 mg/ml CMD (Carboxymethyldextran, Fluka). In one embodiment a mouse antibody capture system was established on the CM5 biosensor. A polyclonal rabbit anti murine IgG Fc capture antibody (RbAMIgG, PAb<M-IgG>Rb-IgG (IS) (BR-1008-38, 2016-12, GE HC) was immobilized at 13kRU according to the manufacturer's instructions using NHS/EDC chemistry.

Anti-TropT antibodies were diluted in sample buffer at 10 nM each and were captured on the biosensor at a flow rate of 10 µl/min for 0.5 min followed by a 0.5 min washing step with 2.5-fold concentrated PBS-DT system buffer at 80 µl/min. The murine antibody Capture Level (CL) in response units (RU) was monitored.

A series of TropT (37 kDa, Roche) analyte concentrations was injected at 80 µl/min for 2 min association phase and 15 min dissociation phase. TropT concentrations were 0 nM, 1.1 nM, 3.3 nM, 10 nM×2, 30 nM and 90 nM. The biosensor capture system was regenerated by a 15 sec injection of 10 mM Glycin pH 1.5 followed by a 2 min injection of 10 mM Glycin pH 1.7 at 20 µl/min.

Sensorgram overlay plots were produced to visualize the TropT binding signal. The Binding Late report points from the signal plateau of the analyte association phase were monitored. Kinetic parameters were determined using the Biacore evaluation software. The kinetic parameters ka [1/Ms], kd [1/s], t1/2 diss [min], KD [M] and the antibody: TropT binding stoichiometry (Molar Ratio) were determined.

The invention claimed is:

1. An antibody conjugate comprising an antibody and a tag, wherein one or more element(s) present in the antibody exhibit an isotope ratio which differs from the naturally occurring isotope ratio of said one or more element(s), wherein the amount of the isotope which is less-common in nature is increased to at least 4% of the atoms of the respective element in the antibody.

2. The conjugate of claim 1, wherein the less common isotope is increased to 6-12% of the atoms of the respective element in the antibody.

3. The conjugate of claim 1, wherein the less common isotope is increased to 6-10% of the atoms of the respective element in the antibody.

4. The conjugate of claim 1, wherein the less common isotope is increased to 8-10% of the atoms of the respective element in the antibody.

5. The conjugate of claim 1, wherein the less common isotope is increased to 30-70% of the atoms of the respective element in the antibody.

6. The conjugate of claim 1, wherein the less common isotope is increased to 40-60% of the atoms of the respective element in the antibody.

7. The conjugate of claim 1, wherein the less common isotope is increased to 50% of the atoms of the respective element in the antibody.

8. The conjugate according to claim 1, wherein the less common isotope is selected from the group consisting of $^{13}C$ of the element Carbon (C), $^{2}H$ of the element Hydrogen (H), $^{15}N$ of the element Nitrogen (N), and $^{17}O$, and/or $^{18}O$ of the element Oxygen (O).

9. The conjugate according to claim 1, wherein the isotope is incorporated in the non-essential amino acids of the antibody.

10. The conjugate according to claim 1, wherein the tag is selected from the group consisting of a partner of a binding pair, a functional group, a therapeutic agent, a cytotoxic agent, a fluorophore, a chemiluminescent tag or an electrochemiluminescent tag, a radioactive tag, a metal chelate complex for imaging or radiotherapeutic purposes, an enzyme, or a fluorescent protein.

11. The conjugate according to claim 1, wherein the tag is a biotin or streptavidin tag.

12. The conjugate according to claim 1, wherein the antibody specifically binds to a biomarker.

13. The conjugate according to claim 12, wherein the biomarker is indicative of a disease.

* * * * *